(12) United States Patent
Au et al.

(10) Patent No.: US 11,923,092 B2
(45) Date of Patent: Mar. 5, 2024

(54) DEEP-LEARNING-BASED FALL DETECTION BASED ON HUMAN KEYPOINTS

(71) Applicant: AltumView Systems Inc., Burnaby (CA)

(72) Inventors: Andrew Tsun-Hong Au, Coquitlam (CA); Dong Zhang, Port Coquitlam (CA); Chi Chung Chan, Burnaby (CA); Jiannan Zheng, Delta (CA)

(73) Assignee: Altum View Systems Inc., Vancouver (CA)

( * ) Notice: Subject to any disclaimer, the term of this patent is extended or adjusted under 35 U.S.C. 154(b) by 190 days.

(21) Appl. No.: 17/534,448

(22) Filed: Nov. 23, 2021

(65) Prior Publication Data
US 2022/0079472 A1     Mar. 17, 2022

Related U.S. Application Data

(63) Continuation of application No. 16/672,432, filed on Nov. 2, 2019, now Pat. No. 11,179,064.

(51) Int. Cl.
*G16H 50/30* (2018.01)
*A61B 5/00* (2006.01)
(Continued)

(52) U.S. Cl.
CPC ............ *G16H 50/30* (2018.01); *A61B 5/1117* (2013.01); *A61B 5/112* (2013.01); *A61B 5/7275* (2013.01);
(Continued)

(58) Field of Classification Search
CPC ...... G16H 50/30; G16H 30/40; A61B 5/1117; A61B 5/112; A61B 5/7275; A61B 5/7264; A61B 5/1116; A61B 5/1123; A61B 5/1127; A61B 5/1176; A61B 5/7267; A61B 2503/08; A61B 5/1128; G06N 3/08; G06N 3/045; G06N 3/044; G06T 3/0093; G06T 11/00; G06T 2210/22; G06V 20/41; G06V 20/52; G06V 40/23; G06V 20/44;
(Continued)

(56) References Cited

U.S. PATENT DOCUMENTS 9,972,187 B1 * 5/2018 Srinivasan ........... G08B 21/043
10,096,223 B1 * 10/2018 Kusens ............. G08B 21/0476
(Continued)

*Primary Examiner* — Christopher M Brandt

(57) ABSTRACT

Various embodiments of a fall-detection system for detecting personal fall while preserving the privacy of a detected person are disclosed. This disclosed fall-detection system can begin by receiving a sequence of video images comprising a person being monitored. The disclosed fall-detection system then processes each video image in the sequence of video images by: detecting the person in the video image; and extracting a skeletal figure of the detected person by identifying a set of human keypoints from the detected person. Next, the disclosed fall-detection system processes the sequence of skeletal figures corresponding to the sequence of video images by labeling each skeletal figure in the sequence of skeletal figures with an action among a set of predetermined actions. The disclosed fall-detection system subsequently generates a fall/non-fall decision for the detected person based on the set of action labels corresponding to the sequence of video images.

20 Claims, 13 Drawing Sheets

(51) Int. Cl.
*A61B 5/11* (2006.01)
*G06N 3/08* (2023.01)
*G06T 3/00* (2006.01)
*G06T 11/00* (2006.01)
*G06V 20/40* (2022.01)
*G06V 20/52* (2022.01)
*G06V 40/20* (2022.01)
*G08B 5/22* (2006.01)
*G08B 21/04* (2006.01)

(52) U.S. Cl.
CPC ............ *G06N 3/08* (2013.01); *G06T 3/0093* (2013.01); *G06T 11/00* (2013.01); *G06V 20/41* (2022.01); *G06V 20/52* (2022.01); *G06V 40/23* (2022.01); *G08B 5/222* (2013.01); *G08B 21/043* (2013.01); *G08B 21/0476* (2013.01); *G06T 2210/22* (2013.01); *G06V 20/44* (2022.01)

(58) Field of Classification Search
CPC ...... G06V 40/10; G06V 40/161; G06V 40/20; G06V 40/172; G08B 5/222; G08B 21/043; G08B 21/0476; G08B 29/186
See application file for complete search history.

(56) References Cited

U.S. PATENT DOCUMENTS

| | | | | |
|---|---|---|---|---|
| 10,140,504 B2* | 11/2018 | Finkelstein | ............ | H04W 12/06 |
| 2004/0001142 A1* | 1/2004 | Kumhyr | ................ | G06V 20/52 |
| | | | | 348/E7.086 |
| 2017/0344832 A1* | 11/2017 | Leung | .................... | G06V 20/52 |
| 2018/0064373 A1* | 3/2018 | Regev | ..................... | G01S 7/539 |
| 2018/0232639 A1* | 8/2018 | Lin | ........................ | G06N 3/063 |
| 2018/0249125 A1* | 8/2018 | Mate | ................... | H04N 7/1675 |
| 2018/0342081 A1* | 11/2018 | Kim | ..................... | A61B 5/1117 |
| 2019/0287376 A1* | 9/2019 | Netscher | ................ | G16H 50/20 |
| 2020/0117901 A1* | 4/2020 | McClernon | ............ | G08B 31/00 |

* cited by examiner

DEEP-LEARNING-BASED FALL DETECTION BASED ON HUMAN KEYPOINTS

PRIORITY CLAIM AND RELATED PATENT APPLICATIONS

This patent application is a continuation of, and hereby claims the benefit of priority under 35 U.S.C. § 120 to co-pending U.S. patent application Ser. No. 16/672,432, filed on 2 Nov. 2019, entitled, "Method and System for Privacy-Preserving Fall Detection," by inventors Him Wai Ng, Xing Wang, Jiannan Zheng, Andrew Tsun-Hong Au, Chi Chung Chan, Kuan Huan Lin, Dong Zhang, Eric Honsch, Kwun-Keat Chan, Adrian Kee-Ley Auk, Karen Ly-Ma, Jianbing Wu, and Ye Lu, which in turn claims the benefit of priority under 35 U.S.C. 119(e) to U.S. Provisional Patent Application No. 62/786,541 entitled "Method and System for Privacy-Preserving Fall Detection," by the same inventors, and filed on Dec. 30, 2018, all of the above-listed applications are incorporated herein by reference as a part of this patent document.

TECHNICAL FIELD

The present disclosure generally relates to the field of medical and health monitoring, and more specifically to systems, devices and techniques for performing highly-reliable and privacy-preserving fall detections on people.

BACKGROUND

As life expectancy worldwide continues to rise, a rapidly aging population has become a serious social problem faced by many countries. An aging population is generally composed of people over 65 years old. As the number of people in this age group is growing rapidly, the ever-increasing demands for quality healthcare services impose significant challenges for the healthcare providers and the society. Of various medical and health problems associated with an aging population, falls are one of the most common but extremely serious problems faced by the elderly people. Elderly people have significantly higher risk of falling which continues to increase with age, and a fall often leads to serious and irreversible medical consequences. However, if a fall does occur, the ability to generate an alert/alarm signal in the first moments after the fall so that medical help can be rendered immediately can have vital importance. Nowadays, such fall alarms can be generated by various fall detection devices which monitor and detect falls for those people with the higher risk of falling.

Various types of fall detection devices have been developed. For example, these fall detection devices include wearable fall-detection devices, which typically rely on using accelerometers or gyroscopes for detecting a fall. However, wearable fall-detection devices need to be worn by the people being monitored most of the time and recharged frequently, thereby making them cumbersome and inconvenient to use. Moreover, many people tend to forget wearing them, and some even refuse to wear them. Some existing wearable fall-detection devices are based on acoustic/vibration sensors. However, these fall-detection devices tend to have lower accuracy, and are generally only useful for detecting heavy impact.

Another type of fall-detection devices uses various vision-based fall-detection techniques, e.g., based on captured videos of a high-risk individual. For example, one existing technique uses a depth camera to detect falls. However, the accuracies of depth cameras are often inadequate for monitoring large areas. In another existing technique, the field of view of a captured video is partitioned into an upper region and a lower region, and a motion event corresponding to a person in the lower region is detected based on the magnitude and the area of the motion. In still another existing technique, fall detection is also performed by using the height and aspect ratio of the person detected in a captured video. However, in the above techniques, the decision rules for identifying a fall are quite naïve and the performances of these system cannot meet desired accuracy requirements.

In another video-based fall-detection system, gradient-based feature vectors are calculated from the video images and used to represent human objects. These feature vectors are subsequently sent to a simple three-layer Elman recurrent neural network (RNN) for fall detection. However, the generally low complexity of this simple RNN architecture also limits the performance of the associated fall detection outcomes.

Recently, convolutional neural network (CNN)-based techniques have been applied to fall detections. These CNN-based techniques are generally more accurate and robust than the above-described techniques that use simple rules or parameters to make falls predictions. For example, one such technique uses CNN-based architectures to identify human actions captured in an image. However, the existing CNN-based fall-detection techniques require significant amount of computational resources and therefore are not suitable for embedded system implementations.

SUMMARY

In this patent disclosure, various embodiments of a privacy-preserving embedded fall-detection vision system (which is also referred to as the "embedded fall-detection system" or simply the "embedded vision system" in this patent disclosure) including various software and/or hardware modules for implementing various vision-based and privacy-preserving fall-detection functionalities are disclosed. Specifically, this embedded fall-detection system is a standalone system that can include hardware modules such as one or more cameras for capturing video images of one or more persons being monitored for potential falls and one or more processors for processing the captured video images. Moreover, this embedded fall-detection system can include various software modules for processing the captured video images and subsequently generating fall-detection output including fall alarms/notifications based on the captured video images. The disclosed embedded fall-detection system can be implemented as a single-unit embedded fall-detection vision sensor. For various fall detection applications, this single-unit embedded fall-detection vision sensor can be installed at a single fixed location for monitoring persons/individuals with high falling risks, such as seniors, people with disabilities, or people with certain illnesses.

Also in this patent disclosure, various embodiments of a distributed privacy-preserving fall-detection system including: one or multiple standalone embedded fall-detection vision sensors implemented based on the disclosed embedded fall-detection system; a server; and an associated mobile application (or "mobile app"), all of which coupled together through a network are disclosed. In some embodiments, this distributed fall-detection system can be implemented as a multi-vision-sensor fall-detection system which is composed of multiple standalone embedded fall-detection vision sensors. The multiple standalone embedded fall-detection vision sensors can be installed at multiple fixed locations different from one another, wherein each of the multiple embedded fall-detection vision sensors can include at least one camera for capturing video images and various software and hardware modules for processing the captured video images and generating corresponding fall-detection output including fall alarms/notifications based on the captured video images.

In various embodiments, the server in the disclosed fall-detection system can be configured to collect and process multiple sources of fall detection outputs generated by the multiple standalone embedded fall-detection vision sensors, select one source of fall-detection output among the multiple sources of outputs, and subsequently transmit the selected source of fall-detection output to the associated fall-detection mobile app installed on one or more mobile devices. In various embodiments, the server can be a cloud-based server or a local server. In various embodiments, the server and the mobile app can also be used to add and remove profiles within the multiple standalone embedded fall-detection vision sensors for people to be monitored or being monitored by the distributed fall-detection system. In such embodiments, the server can be used to distribute information to the multiple standalone embedded fall-detection vision sensors. In some embodiments, the disclosed distributed fall-detection system is composed of a single embedded fall-detection vision sensors (instead of multiple embedded fall-detection vision sensors), the server, and the mobile app.

In various embodiments, to preserve the privacies of people being monitored or captured by either the disclosed embedded fall-detection system or the disclosed distributed fall-detection system, all fall-detection-related computations on captured video images are performed in-situ inside the embedded fall-detection system or each of the standalone embedded fall-detection vision sensors within the distributed fall-detection system. In some embodiments, after processing the captured video images in-situ, each embedded fall-detection vision sensor of the disclosed distributed fall-detection system only transmits sanitized video images and/or video clips (e.g., by transmitting only the keypoints/skeleton/stick figure representations of each detected person instead of the actual images of the detected person) to the server of the distributed fall-detection system along with fall alarms/notifications. This privacy-preserving feature of the disclosed embedded fall-detection system can be enabled by the recent developments of various powerful artificial intelligence (AI) integrated circuit (IC) chips which can be easily integrated with the disclosed embedded fall-detection system.

In one aspect, a process for performing person fall detection is disclosed. This process can begin by receiving a sequence of video images including a person being monitored. Next, for each image in the sequence of video images, the process first detects a pose of the person within the image, and then classifies the pose of the detected person within the image into an action among a set of predetermined actions. Next, the process aggregates the sequence of classified actions for the detected person corresponding to the sequence of video images. The process subsequently processes the aggregated sequence of classified actions to determine if a fall has occurred.

In some embodiments, the process detects a pose of the person within the image by first identifying a set of locations within the image corresponding to a set of human keypoints of the person. The process then connects neighboring locations in the set of identified locations to form a skeleton diagram of the person, wherein the skeleton diagram represents a sanitized image of the detected person.

In some embodiments, the process classifies the pose of the detected person into an action among the set of predetermined actions by: cropping out from the image, a two-dimensional (2-D) image of the detected person based on the skeleton diagram of the detected person; feeding the cropped image of the detected person into an action classifier configured to predict probabilities of the detected person being in each of the set of predetermined actions; and classifying the pose of the detected person into the action based on the set of probabilities corresponding to the set of predetermined actions.

In some embodiments, the set of predetermined actions includes a first category of actions and a second category of actions, and the process classifies the pose of the detected person into an action among the set of predetermined actions by first classifying the pose of the detected person into either the first category of actions or the second category of actions. Next, for the classified first or second category of actions, the process further classifies the pose of the detected person into a predetermined action among the classified category of actions. In some embodiments, the first category of actions is a subset of dangerous actions among the set of predetermined actions, wherein the subset of dangerous actions includes one or more of: a lying action and a struggling action; and the second category of actions is a subset of normal actions among the set of predetermined actions, wherein the subset of normal actions includes one or more of: a standing action, one or more types of sitting actions, a bending action, and a squatting action.

In some embodiments, the process aggregates the sequence of classified actions for the detected person corresponding to the sequence of video images by: identifying a dangerous region, such as a floor or a carpet in the sequence of video images; determining a spatial relationship between each of the sequence of classified actions and the identified dangerous region; and when a classified dangerous action among the sequence of classified actions is determined to be within the identified dangerous region, confirming the classified dangerous action.

In some embodiments, the process aggregates the sequence of classified actions for the detected person corresponding to the sequence of video images by: identifying a normal region, such as a bed or a sofa in the sequence of video images; determining a spatial relationship between each of the sequence of classified actions and the identified normal region; and when a classified dangerous action among the sequence of classified actions is determined to be within the identified normal region, reclassifying the classified dangerous action as a normal action.

In some embodiments, the process processes the aggregated sequence of classified actions to determine if a fall has occurred by using a state machine to detect a fall associated with the aggregated sequence of classified actions, wherein the state machine includes at least a normal state representing normal activities and a warning state indicative of a fall.

In some embodiments, the process processes the aggregated sequence of classified actions using the state machine to detect a fall by first determining a current state and an associated state score for the detected person in the state machine. Next, the process sequentially processes the aggregated sequence of classified actions as follows. For each classified action classified as a dangerous activity, the process increases the state score of the current state in the state machine to obtain an updated state score of the current state, and if the updated state score of the current state exceeds a predetermined upper threshold, the process causes the state machine to transition from the current state toward the warning state. However, for each classified action classified as a normal activity, the process decreases the state score of the current state in the state machine to obtain an updated state score of the current state, and if the updated state score of the current state drops below a predetermined lower threshold, the process causes the state machine to transition from the current state away from the warning state.

In some embodiments, if a fall is detected for the person, the process further includes: generating a fall alarm; generating a sanitized video clip depicting the fall by replacing the actual images of the detected person in the sequence of video images with the skeleton diagrams of the detected person; and transmitting the sanitized video clip along with the fall alarm to a server, thereby preserving the privacy of the detected person.

In some embodiments, if a fall is detected for the person, the process further includes generating a sanitized video clip by: identifying a common background image for the sequence of video images; and superimposing the set of skeleton diagrams of the detected person corresponding to the sequence of video images onto the common background image to obtain a sequence of sanitized video images. Next, the process transmits the sanitized video clip composed of the sequence of sanitized video images to a server, thereby preserving the privacy of the detected person.

In another aspect, a fall-detection system is disclosed. This fall-detection system can include: one or more processors and a memory coupled to the one or more processors. The fall-detection system can also include: a pose-estimation module configured to receive a sequence of video images including a person being monitored and detect a pose of the person within each image in the sequence of video images; an action-recognition module configured to classify, for each image in the sequence of video images, the pose of the detected person within the image into an action among a set of predetermined actions; and a fall-detection module configured to aggregate the sequence of classified actions for the detected person corresponding to the sequence of video images and process the aggregated sequence of classified actions to determine if a fall has occurred.

In some embodiments, the pose estimation module is configured to detect a pose of the person within the image by: identifying a set of locations within the image corresponding to a set of human keypoints of the person; and connecting neighboring locations in the set of identified locations to form a skeleton diagram of the person, wherein the skeleton diagram represents a sanitized image of the detected person.

In some embodiments, the action-recognition module is configured to classify the pose of the detected person into an action among the set of predetermined actions by: cropping out from the image, a two-dimensional (2-D) image of the detected person based on the skeleton diagram of the detected person; feeding the cropped image of the detected person into an action classifier configured to predict probabilities of the detected person being in each of the set of predetermined actions; and classifying the pose of the detected person into the action based on the set of probabilities corresponding to the set of predetermined actions.

In some embodiments, the fall-detection module is configured to aggregate the sequence of classified actions corresponding to the sequence of video images by: identifying a normal region, such as a bed or a sofa in the sequence of video images; determining a spatial relationship between each of the sequence of classified actions and the identified normal region; and when a classified dangerous action among the sequence of classified actions is determined to be within the identified normal region, reclassifying the classified dangerous action as a normal action.

In some embodiments, the fall-detection module is configured to process the aggregated sequence of classified actions by using a state machine to detect a fall associated with the aggregated sequence of classified actions, wherein the state machine includes at least a normal state representing normal activates and a warning state indicative of a fall.

In some embodiments, the fall-detection module is configured to process the aggregated sequence of classified actions using the state machine by: for each classified action classified as a dangerous activity, increasing the state score of the current state in the state machine to obtain an updated state score of the current state, wherein if the updated state score of the current state exceeds a predetermined upper threshold, causing the state machine to transition from the current state toward the warning state; and for each classified action classified as a normal activity, decreasing the state score of the current state in the state machine to obtain an updated state score of the current state, wherein if the updated state score of the current state drops below a predetermined lower threshold, causing the state machine to transition from the current state away from the warning state.

In yet another aspect, an embedded fall-detection system is disclosed. This embedded fall-detection system includes: one or more cameras configured to capture a sequence of video images including a person; one or more processors; and a memory coupled to the one or more processors. The memory stores instructions that, when executed by the one or more processors, cause the system to: receive the sequence of video images; detect a pose of the person within each image in the sequence of video images; classify, for each image in the sequence of video images, the pose of the detected person within the image into an action among a set of predetermined actions; aggregate the sequence of classified actions for the detected person corresponding to the sequence of video images; and process the aggregated sequence of classified actions to determine if a fall has occurred.

In some embodiments, a state machine is used to detect a fall associated with the aggregated sequence of classified actions, wherein the state machine includes at least a normal state representing normal activates and a warning state indicative of a fall. The memory further stores instructions that, when executed by the one or more processors, cause the system to: determine a current state and an associated state score for the detected person in the state machine and sequentially process the aggregated sequence of classified actions as follows: for each classified action classified as a dangerous activity, increasing the state score of the current state in the state machine to obtain an updated state score of the current state, wherein if the updated state score of the current state exceeds a predetermined upper threshold, causing the state machine to transition from the current state toward the warning state; and for each classified action classified as a normal activity, decreasing the state score of the current state in the state machine to obtain an updated state score of the current state, wherein if the updated state score of the current state drops below a predetermined lower threshold, causing the state machine to transition from the current state away from the warning state.

Other features and advantages of the present inventive concept should be apparent from the following description which illustrates by way of example aspects of the present inventive concept.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

The following description is presented to enable any person skilled in the art to make and use the embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

Terminology

Figure 1:
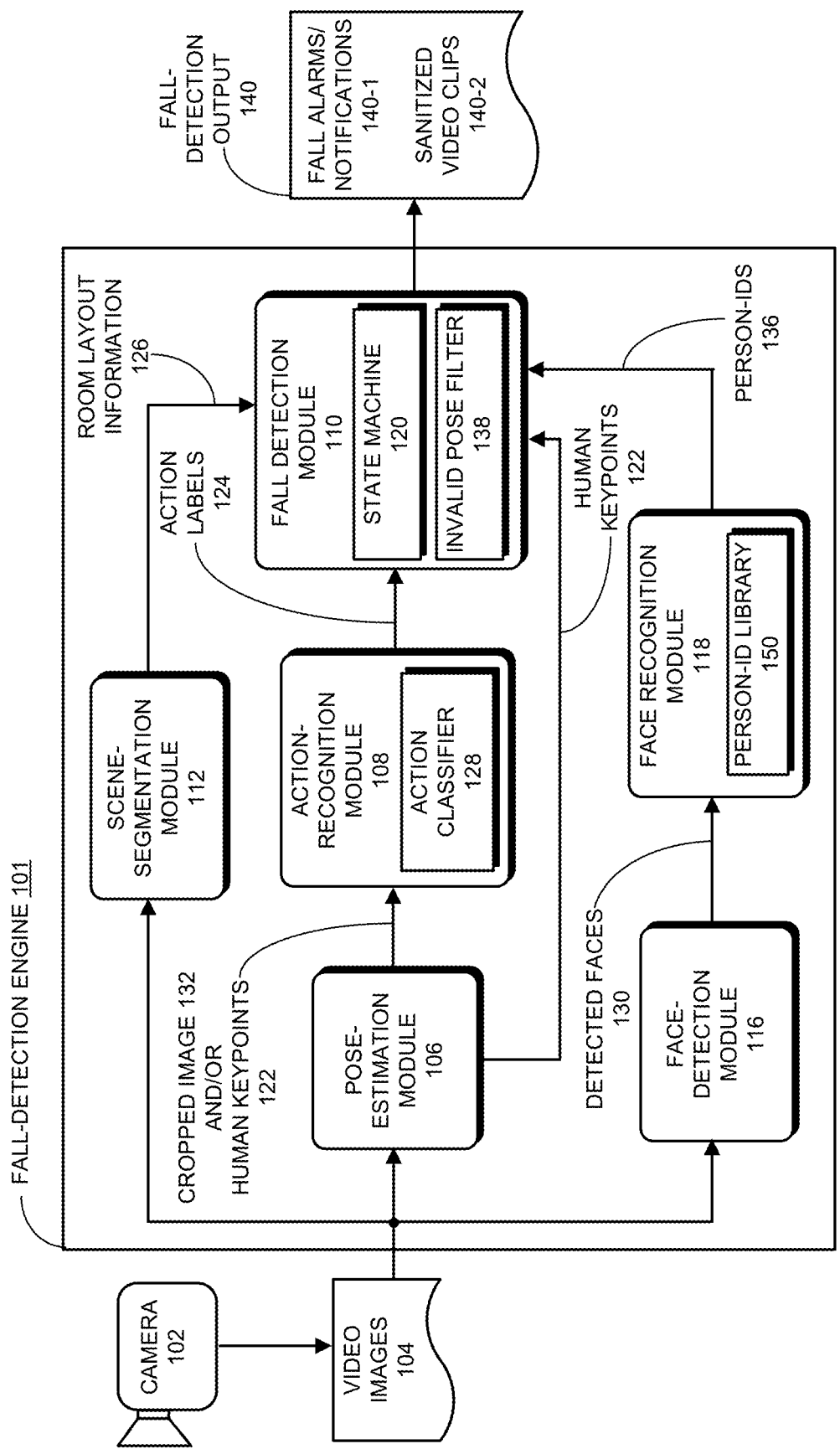
FIG. 1 illustrates a block diagram of the disclosed embedded fall-detection system in accordance with some embodiments described herein.

Throughout this patent disclosure, the terms "embedded fall-detection vision system," "embedded fall-detection system," and "embedded vision system" are used interchangeably to refer to the embedded fall-detection system 100 described in conjunction with FIG. 1. The terms "embedded fall-detection vision sensor" and "embedded vision sensor" are used interchangeably to refer to a standalone fall-detection device/unit which integrates embedded fall-detection system 100 inside a hardware environment. Moreover, the term "distributed fall-detection system" refers to an overall fall-detection system described in conjunction with FIG. 2 which includes: one or more "embedded fall-detection vision sensors" implemented based on the "embedded fall-detection system," a server, and a mobile application.

Proposed Fall-Detection System Overview

Aging population is a problem faced by many countries. Elderly people have higher risk of falling, and a fall often leads to serious medical consequences. Hence, it is desirable to provide fall detection systems and techniques to monitor and detect falls for those people with high-risk of falling. Furthermore, it is also desirable to preserve the privacy of the people being monitored.

In this patent disclosure, various embodiments of an embedded privacy-preserving fall-detection vision system including various software and/or hardware modules for implementing various image-based and privacy-preserving fall-detection functionalities are disclosed. In the discussions below, this embedded fall-detection vision system is also referred to as the "embedded fall-detection system" or the "embedded vision system." Note that this embedded fall-detection system can operate as a standalone fall-detection system to monitor and detect falls. Specifically, this embedded fall-detection system can include hardware modules such as one or more cameras for capturing video images of one or more persons being monitored for potential falls and one or more processors for processing the captured video images. Moreover, this embedded fall-detection system can include various software modules for processing the captured video images and subsequently generating fall-detection output including fall alarms/notifications based on the captured video images. The disclosed embedded fall-detection system can be implemented as a single-unit embedded fall-detection vision sensor. For various fall detection applications, this single-unit embedded fall-detection vision sensor can be installed at a single fixed location for monitoring persons/individuals with high falling risks, such as seniors, people with disabilities, or people with certain illnesses. Moreover, in the discussions below, the term "fall-detection engine" will be introduced to refer to the portion of the embedded fall-detection system that only includes the various computer software modules for implementing one or more disclosed fall-detection techniques, but does not include any hardware module such as a processor or a camera.

Also in this patent disclosure, various embodiments of a distributed privacy-preserving fall-detection system including: one or multiple standalone embedded fall-detection vision sensors implemented based on the disclosed embedded fall-detection system; a server; and an associated mobile application (or "mobile app"), all of which coupled together through a network are disclosed. In some embodiments, this distributed fall-detection system can be implemented as a multi-vision-sensor fall-detection system which is composed of multiple standalone embedded fall-detection vision sensors. These multiple standalone embedded fall-detection vision sensors can be installed at multiple fixed locations different from one another, wherein each of the multiple embedded fall-detection vision sensors can include at least one camera for capturing video images and various software and hardware modules for processing the captured video images and generating corresponding fall-detection output including fall alarms/notifications based on the captured video images.

In various embodiments, the server in the disclosed distributed fall-detection system can be configured to collect and process multiple sources of fall detection outputs generated by the multiple standalone embedded fall-detection vision sensors, select one source of fall-detection output among the multiple sources of outputs, and subsequently transmit the selected source of fall-detection output to the associated fall-detection mobile app installed on one or more mobile devices. In various embodiments, the server can be a cloud-based server or a local server. In various embodiments, the server and the mobile app can also be used to add and remove profiles within the multiple standalone embedded fall-detection vision sensors for people to be monitored or being monitored by the distributed fall-detection system. In such embodiments, the server can be used to distribute information to the multiple standalone embedded fall-detection vision sensors. In some embodiments, the disclosed distributed fall-detection system is composed of a single embedded fall-detection vision sensor (instead of multiple embedded fall-detection vision sensors), the server, and the mobile app.

In various embodiments, to preserve the privacies of people being monitored or captured by either the disclosed embedded fall-detection system or the disclosed distributed fall-detection system, all fall-detection-related computations on captured video images are performed in-situ inside the embedded fall-detection systems or each of the standalone embedded fall-detection vision sensors within the distributed fall-detection system. In some embodiments, after processing the captured video images in-situ, each embedded fall-detection vision sensor of the disclosed distributed fall-detection system only transmits sanitized video images and/or video clips (e.g., by transmitting only the keypoints/skeleton/stick figure representations of each detected person instead of the actual images of the detected person) to the server of the distributed fall-detection system along with fall alarms/notifications. This privacy-preserving feature of the disclosed embedded fall-detection system can be enabled by the recent developments of various powerful artificial intelligence (AI) integrated circuit (IC) chips which can be easily integrated with the disclosed embedded fall-detection system. One example of such AI chips is the HiSilicon Hi3559A System on Chip (SoC), which includes 2 ARM Cortex A73 CPUs, 3 ARM Cortex A53 CPUs, a dual-core ARM Mali G71 GPU, a dual-core Neural Network Inference Acceleration Engine (NNIE), and a quad-core DSP module. Note that this particular SoC also includes built-in security, signature verification, and tamper-proofing functionalities.

Note that various embodiments of the disclosed embedded fall-detection system are based on implementing various deep-learning-based fast neural networks while combining various optimization techniques, such as network pruning, quantization, and depth-wise convolution. As a result, the disclosed embedded fall-detection system can perform a multitude of deep-learning-based functionalities such as real-time deep-learning-based pose estimation, action recognition, fall detection, face detection, and face recognition. FIG. 1 illustrates a block diagram of the disclosed embedded fall-detection system 100 in accordance with some embodiments described herein.

As can be seen in FIG. 1, embedded fall-detection system 100 includes a fall-detection engine 101 and a camera 102. Fall-detection engine 101 further includes various fall-monitoring and fall-detection functional modules including: a pose-estimation module 106, an action-recognition module 108, a fall-detection module 110, a scene-segmentation module 112, a face-detection module 116, and a face-recognition module 118. However, other embodiments of the disclosed embedded fall-detection system can include additional functional modules or omit one or more of the functional modules shown in embedded fall-detection system 100 without departing from the scope of the present disclosure. Exemplary implementations of the various functional modules of embedded fall-detection system 100 are described further below.

Embedded fall-detection system 100 can use camera 102 to monitor human activities within a given space such as a room, a house, a lobby, or a hallway, and to capture video images and/or still images which can be used for fall analysis and prediction. In some embodiments, when embedded fall-detection system 100 is active, camera 102 generates and outputs video images 104 which can includes video images of one or multiple persons present in the monitored space. Fall-detection engine 101 receives video images 104 as input and subsequently processes input video images 104 and makes fall/non-fall predictions/decisions based on the processed video images 104. Embedded fall-detection system 100 can generate fall-detection output 140 including fall alarms/notifications 140-1 and sanitized video clips 140-2 when human falls are detected. However, embedded fall-detection system 100 can also output activities of daily living (ADLs) statistics for a monitored person even when no fall is detected. Note that camera 102 does not have to be a part of embedded fall-detection system 100 but rather a part of an overall embedded fall-detection device referred to as the "embedded fall-detection vision sensor" below. When embedded fall-detection system 100 only includes fall-detection engine 101 without any additional hardware component, embedded fall-detection system 100 can be implemented entirely in computer software.

In some embodiments, embedded fall-detection system 100 of FIG. 1 can be implemented as an embedded fall-detection vision sensor (also referred to as an "embedded vision sensor" hereinafter). In these embodiments, various functional modules of the fall-detection engine 101 (i.e., pose-estimation module 106, action-recognition module 108, fall-detection module 110, scene segmentation module 112, face-detection module 116, and face-recognition module 118) are integrated into the embedded fall-detection vision sensor. This embedded fall-detection vision sensor can use one or more cameras, such as camera 102 to monitor a space such as a room, a house, a lobby, or a hallway to detect falls, and use fall-detection engine 101 to process captured video images and to generate fall-detection output 140 including both fall alarms/notifications 140-1 and sanitized video clips 140-2. More specifically, this embedded fall-detection vision sensor can include one or more memories for storing instructions for implementing fall-detection engine 101, one or more processors including CPUs and/or neural processing units (NPUs) for executing the instructions from the one or more memories to implement the various functional modules of fall-detection engine 101. Moreover, this embedded fall-detection vision sensor can also include one or more cameras, one or more sensors, and a network interface, among others. When implemented as a single-unit fall-detection and monitoring device, this embedded fall-detection vision sensor will also include a housing/enclosure, one or more attachment mechanisms, and possibly a stand/base. More detailed implementations of an embedded fall-detection vision sensor are described below in conjunction with FIG. 10.

Figure 2:
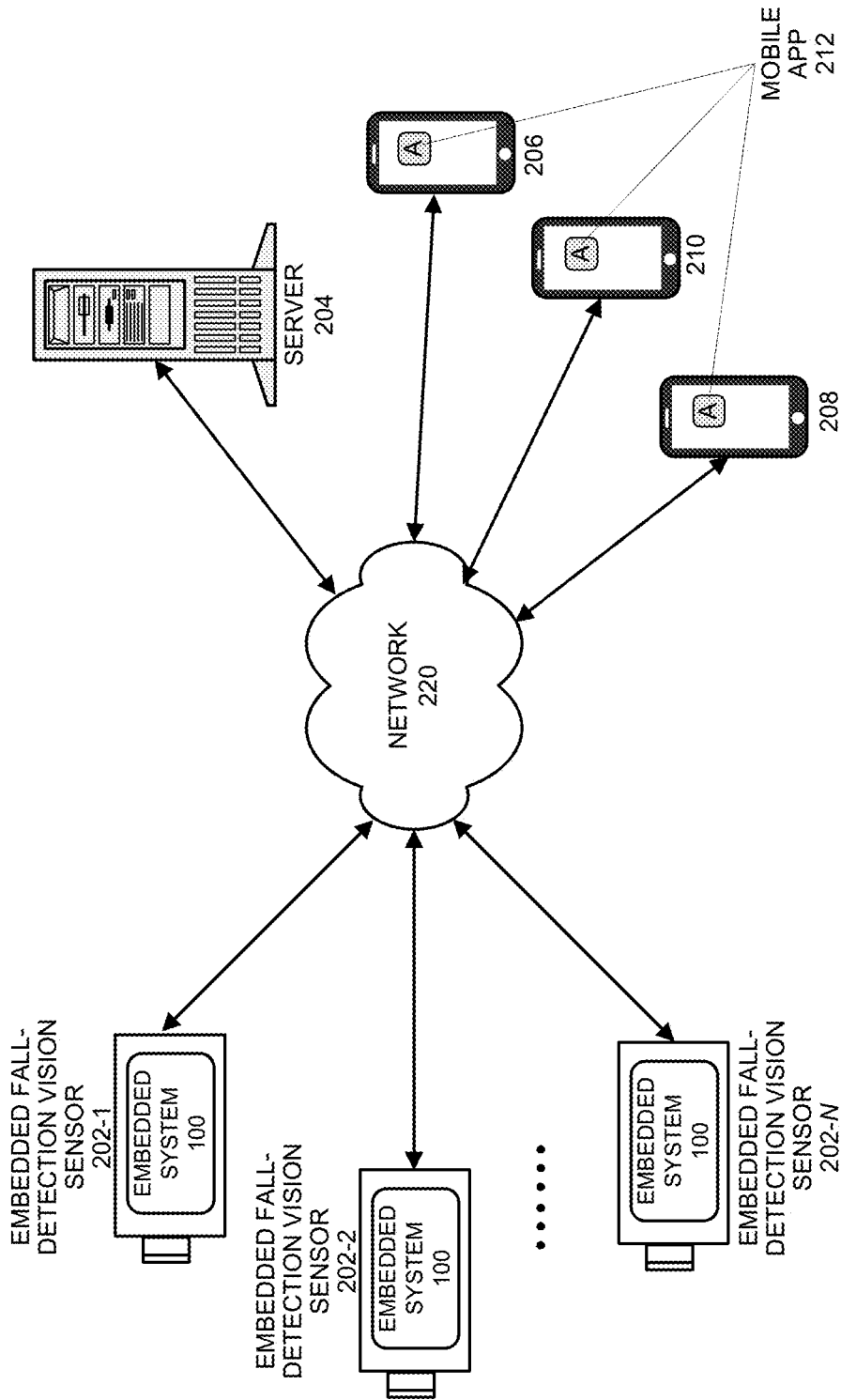
FIG. 2 illustrates a block diagram of the disclosed distributed fall-detection system including one or multiple embedded fall-detection vision sensors based on the embedded fall-detection system of FIG. 1 in accordance with some embodiments described herein.

FIG. 2 illustrates a block diagram of a disclosed distributed fall-detection system 200 including one or multiple embedded fall-detection vision sensors based on embedded fall-detection system 100 of FIG. 1 in accordance with some embodiments described herein. More specifically, each of the one or multiple embedded fall-detection vision sensors 202-1, 202-2, . . . , and 202-N is a standalone fall-detection unit implemented based on the above-described embedded fall-detection system 100 of FIG. 1. In other words, each embedded fall-detection vision sensor 202 within distributed fall-detection system 200 includes embedded fall-detection system 100 or otherwise integrates embedded fall-detection system 100 in its entirety. Note that each embedded fall-detection vision sensor 202 can be configured to perform independent fall-monitoring and fall-detection functionalities. In some embodiments, distributed fall-detection system 200 includes only one embedded fall-detection vision sensor 202-1 (i.e., N=1). In these embodiments, distributed fall-detection system 200 can include just one camera for capturing video images of one or more persons being monitored and just one fall detection engine 101 for processing the captured video images to detect falls for the one or more persons.

In some other embodiments, distributed fall-detection system 200 includes more than one embedded fall-detection vision sensor (i.e., N>1). Note that because a single camera can have an associated blind zone, it can be difficult to use such a single-camera embedded fall-detection system to monitor certain large areas. Hence, for fall-monitoring and fall-detection in a large area, distributed fall-detection system 200 including multiple embedded fall-detection vision sensors 202 installed at multiple locations within the large area can be used to eliminate such blind zones, thereby improving the robustness of the overall fall-detection performance. As mentioned above, each of the multiple embedded fall-detection vision sensors 202-1, 202-2, . . . , and 202-N (N>1) is a standalone fall-detection unit implemented based on embedded fall-detection system 100 of FIG. 1.

Note that each of the multiple embedded vision sensors 202 is coupled to server 204 through network 220. In various embodiments, server 204 can be a cloud-based server or a local server. Server 204 itself is further coupled to a number of mobile devices 206, 208, and 210, which can monitored by caregivers and/or medical personnel, via network 220. Server 204 can be communicatively coupled to a client application, such as a fall-detection mobile app 212 (or simply "mobile app 212") installed on each of the mobile devices 206, 208, and 210. In some embodiments, mobile app 212 on a given mobile device is configured to receive from server 204, fall alarms/notifications along with sanitized video clips outputted by the multiple embedded vision sensors 202-1, 202-2, . . . , and 202-N, via network 220. In some embodiments, server 204 can also host a multi-camera management application which is configured to divide each monitored area into a set of zones, and assign one or more embedded vision sensors 202-1, 202-2, . . . , and 202-N to monitor each zone in the set of zones.

As mentioned above, server 204 can be configured to divide a large monitored area into a set of zones, wherein each zone in the set of zones can be covered by two or more embedded vision sensors 202-1, 202-2, . . . , and 202-N (N>1). Moreover, for each zone in the set of zones, server 204 can be configured to "fuse" or otherwise combine fall-detection outputs from two or more embedded vision sensors 202 covering the given zone. For example, if a monitored person's identity cannot be identified or determined based on fall-detection output from a first embedded vision sensor positioned at a bad angle, that person's identity may be identified or determined based on fall-detection output from a second embedded fall-detection vision sensor positioned at a good angle. Generally speaking, server 204 can combine two or more sources of fall-detection outputs from two or more embedded vision sensors 202-1, 202-2, . . . , and 202-N and make a collective fall-detection decision on a given person based on the two or more sources of fall-detection outputs.

More specifically, if a given person's fall in a monitored area is detected by two or more embedded vision sensors 202, each of the two or more embedded vision sensors can send a respective fall alarm/notification 140-1 and a sanitized video clip 140-2 (e.g., using a skeleton/stick-figure representation of the detected person instead of the actual image of the detected person) depicting the falling process to server 204. In some embodiments, the sanitized video clip includes video images buffered for a predetermined amount of time (e.g., 10-15 seconds) immediately before the fall is detected. Hence, the video clip can include a sequence of video images depicting the entire process of falling.

Note that when server 204 receives multiple sources of fall detection outputs from the two or more embedded vision sensors 202, server 204 is configured to determine if the multiple sources of fall detection outputs belong to the same person. If so, server 204 can then select one source of fall detection output among the multiple sources of fall-detection outputs having the highest confident level/score. In some embodiment, this confident score can be embedded in each source of the fall detection output. As will be described further below, both pose-estimation module 106 and action-recognition module 108 in embedded fall-detection system 100 can generate probabilities for the estimated poses and the classified actions for each detected person. As such, a confident score of a generated fall alarm can be determined based on these probability values. Hence, server 204 can select the source of data among the multiple sources associated with the highest confident score and subsequently transmit the selected source of fall-detection output including the associated fall alarm/notification and associated sanitized video clip to fall-detection mobile app 212 installed on mobile devices 206-210. However, when server 204 receives only one source of fall detection output from a single vision sensor among the two or more embedded vision sensors 202, server 204 can directly transmit the received single source of fall-detection output to fall-detection mobile app 212 installed on mobile devices 206-210.

In some embodiments, after receiving the fall-detection output from server 204, mobile app 212 can play the received sanitized video clip on one or more mobile devices 206-210 of one or more caregivers. The disclosed mobile app 212 can also be configured to assist adding or removing profiles of persons to be tracked by the disclosed distributed fall-detection system 200. In some embodiments, a profile of a person can include the person's identity such as person's name, as well as profile photos of the person. In some embodiments, prior to performing fall detection on a person, a profile of the person can be constructed and stored both on server 204 and on each embedded fall-detection vision sensor 202. For example, mobile app 212 can be used to construct a new profile of the person by combining the identity of the person with one or multiple profile photos of the person. In some embodiments, mobile app 212 can be used to take the one or multiple profile photos of the person. Mobile app 212 can then send the profile of the person including the one or multiple profile photos and the person's identity, such as the name of the person to server 204.

Next, at server 204, a profile-management program can be used to generate and assign a unique person-ID for the person (e.g., based on the unique identity of the person) and associated the person-ID with the one or multiple profile photos. In some embodiments, the person-ID of the person generated by server 204 can be a unique numerical value (e.g., an integer value) without any identity information of the person. Hence, the disclosed person-ID can facilitate protecting the privacy of the person. Server 204 can then send the newly generated person-ID of the person along with the profile photos of the person to embedded fall-detection system 100, which maintains a person-ID dictionary. Next, embedded fall-detection system 100 can generate a new entry for the person based on the received person-ID and the profile photos, and add this new entry in the person-ID dictionary.

In some embodiments, server 204 can be a single computing device such as a computer server. In other embodiments, server 204 can represent more than one computing device working together to perform the actions of a server computer, e.g., as a cloud server. Server 204 can include one or more processors and a data storage device. These one or more processors can execute computer instructions stored in the data storage device to perform the various disclosed functions of server 204. Network 220 can include, for example, any one or more of a personal area network (PAN), a local area network (LAN), a campus area network (CAN), a metropolitan area network (MAN), a wide area network (WAN), a broadband network (BBN), the Internet, and the like. Furthermore, network 220 can include, but is not limited to, any one or more of the following network topologies, including a bus network, a star network, a ring network, a mesh network, a star-bus network, tree or hierarchical network, and the like.

Referring back to FIG. 1 but in collaboration with FIG. 2, note that when a person's fall is detected by embedded fall-detection system 100, the embedded fall-detection system can send fall alarm/notification 140-1 along with sanitized video clip 140-2 depicting the falling action to a server, such as server 204 in FIG. 2. Specifically, this sanitized video clip can use a keypoints/skeleton/stick-figure representation of the detected person to replace the actual image of the detected person in each video image. In some embodiments, the sanitized video clip 140-2 can include video images buffered for a predetermined amount of time (e.g., 10-15 seconds) immediately before the fall is detected. Hence, sanitized video clip 140-2 can include a sequence of video images depicting the entire process of falling.

In some embodiments, embedded fall-detection system 100 can track the detected person through the sequence of video images using face-detection module 116, and face-recognition module 118. To facilitate tracking each unique person through a sequence of video frames, embedded fall-detection system 100 can identify and subsequently associate each detected person with a corresponding person-ID stored in the above-described person-ID dictionary (described in more detail below). Embedded fall-detection system 100 can then transmit the identified person-ID along with other fall-detection data associated with the detected person to the server. After receiving the fall-detection output of the detected person including the fall alarm/notification 140-1, the associated sanitized video clip 140-2, and the associated person-ID 136 (if the person is identified), the server, such as server 204 can transmit the above fall-detection data to an associated fall-detection mobile app (e.g., mobile app 212) installed on one or more mobile devices (e.g., mobile device 206-210).

Note that embedded fall-detection system 100 can perform fall detection on a person with or without an associated person-ID. In other words, once a person is detected in the input video images 104, embedded fall-detection system 100 will perform fall detection on the detected person and generate fall alarms/notifications when necessary, even if the detected person does not have an established person-ID or the system fails to identify the detected person. As mentioned above and will be described in more detail below, embedded fall-detection system 100 can include a person-ID dictionary which stores a set of established person-IDs of a group of people that can be tracked by embedded fall-detection system 100. For example, this person-ID dictionary (i.e., person-ID dictionary 150) can be integrated with face-recognition module 118.

In some embodiments, if the detected person doesn't match any stored person-ID in person-ID dictionary 150, then embedded fall-detection system 100 can generate and output the fall alarm/notification 140-1 along with an "unknown person" tag. However, if embedded fall-detection system 100 can successfully match the detected person to an established person-ID in person-ID dictionary 150, then embedded fall-detection system 100 can generate and transmit fall alarm/notification 140-1 along with the identified person-ID 136 of the detected person to the server, such as server 204. After receiving fall alarm/notification 140-1 with the associated person-ID, server 204 can translate the person-ID to an actual identity of the detected person, such as the name of the person, and associate the fall alarm/notification with the actual identity of the detected person. Server 204 can then transmit the selected fall alarm/notification and the identity of the detected person to mobile app 212.

We now describe each of the functional modules of fall-detection engine 101 within the disclosed embedded fall-detection system 100 in more details below.

Pose-Estimation Module

In some embodiments, embedded fall-detection system 100 monitors human motions or actions and predicting falls by first estimating the pose of each person captured in a given video image/frame using pose-estimation module 106 in FIG. 1. As can be seen in FIG. 1, pose-estimation module 106 can receive and process input video images/frames 104 prior to action recognition model 108 and fall-detection module 110. Pose-estimation module 106 next identifies humans captured in the video images 104. For each detected person, pose-estimation module 106 subsequently determines a pose for the detected person. In some embodiments, pose-estimation module 106 can first identify a set of human keypoints 122 (or simply "human keypoints 122" or "keypoints 122") for the detected person within an input video image 104, and then represent a pose of the detected person using the configuration and/or localization of the set of keypoints, wherein the set of keypoints 122 can include, but are not limited to: the eyes, the nose, the ears, the chest, the shoulders, the elbows, the wrists, the knees, the hip joints, and the ankles of the person. In some embodiments, instead of using a full set of keypoints, a simplified set of keypoints 122 can include just the head, the shoulders, the arms, and the legs of the detected person. A person of ordinary skill in the art can easily appreciate that a different pose of the detected person can be represented by a different geometric configuration of the set of keypoints 122.

To implement the above-described functions of pose-estimation module 106 in FIG. 1, various CNN-based techniques for performing human pose estimation can be used. In some embodiments, "bottom-up"-based pose-estimation techniques, such as "OpenPose" (described in "*Realtime Multi-Person 2D Pose Estimation Using Part Affinity Fields*," by Cao et al., CVPR 2017) can be used. These pose-estimation techniques first use a strong CNN-based feature extractor to extract visual features from an input image, and then use a two-branch multi-stage CNN to detect various human keypoints within the input image. Next, the pose-estimation techniques perform a set of bipartite matching operations to "assemble" or connect the detected keypoints into full-body poses for some or all people detected in the image. This type of bottom-up pose-estimation techniques can have both high performance and low complexity, and can also estimate a "probability" of each detected keypoint. Here the probability of a detected keypoint represents a confidence score assigned to the detected keypoint by the pose-estimation model. Typically, under more difficult detection conditions such as poor lighting, confusing background, or obstacles in front of a detected person, the confidence score or the probability of each detected keypoint will be relatively low. For example, if a person wears clothing having very similar color to the background (e.g., white shirt against a white wall), it would be more difficult for the pose-detection algorithm to identify the correct keypoints and their associated locations. In this scenario, the pose-detection algorithm will generate lower probabilities for the uncertain keypoint detections.

Figure 3:
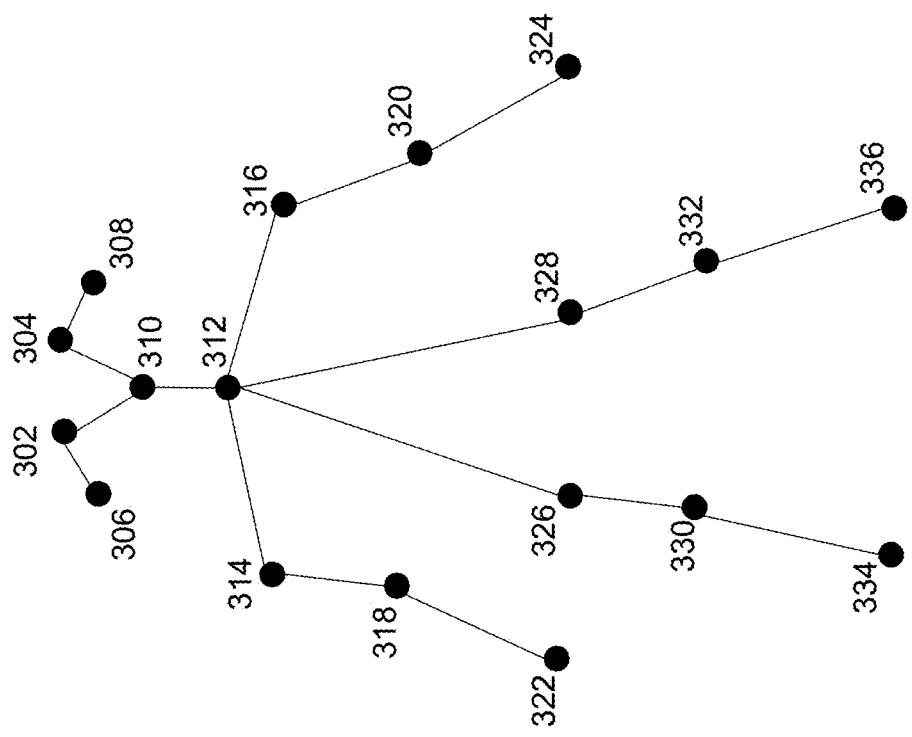
FIG. 3 shows an exemplary skeleton diagram of a detected person in a video image obtained by connecting 18 neighboring keypoints with straight lines in accordance with some embodiments described herein.

In some embodiments, a skeleton diagram of a detected person in an input video image 104 can be obtained by connecting neighboring keypoints representing the detected person with straight lines. FIG. 3 shows an exemplary skeleton diagram 300 of a detected person in a video image obtained by connecting 18 keypoints with straight lines in accordance with some embodiments described herein. As can be seen in FIG. 3, skeleton diagram 300 comprises 18 keypoints corresponding to the two eyes 302 and 304, two ears 306 and 308, nose 310, neck 312, two shoulders 314 and 316, two elbows 318 and 320, two wrists 322 and 324, two hips 326 and 328, two knees 330 and 332, and two ankles 334 and 336 of the detected person, and the resulting skeleton diagram 300 includes 17 line segments connecting these keypoints.

In some embodiments, to allow bottom-up pose-estimation models to run in real-time with optimized performance on embedded systems/devices such as embedded fall-detection system 100, the proposed pose-estimation module 106 implements a bottom-up pose-estimation framework with a number of improvements to the existing framework. Some of these modifications/improvements include:

Replacing the commonly used complex VGG16 network (described in "*Very Deep Convolutional Networks for Large-Scale Image Recognition*," Simonyan et al., arXiv: 1409.1556) with a faster VGG16×4 network (described in "*Channel Pruning for Accelerating Very Deep Neural Networks*," He et al., ICCV 2017 and "*AMC: AutoML for Model Compression and Acceleration on Mobile Devices*," He et al., ECCV 2018) as the backbone/feature extractor, which has an inference speed 4× faster than the VGG16 network. Note that the term "backbone" herein refers to the neural network which receives an input image and extracts image features for use in subsequent deep-learning tasks such as classification, regression, and segmentation. This speed-up is largely due to performing channel pruning, i.e., reducing the width of the feature map, which in turn shrinks the network into a thinner one;

Reducing the number of stages in the two-branch multi-stage CNN;

Reducing each convolution layer filter size to 3×3 in the multi-stages. Although the existing network and the modified network have substantially the same receptive field size, the modified network can be executed much more efficiently;

Quantizing the network parameters and run the network inference in 8-bit integer precision instead of the typical 32-bit floating-point precision. This modification not only reduces the memory usage and the frequency of memory access, it also significantly speeds up the arithmetic computations, making it particularly useful and desirable for resource-limited embedded system applications; and During the network training, applying data augmentation to improve the pose estimation performance for different imaging capturing angles. Note that as a person falls onto the floor, the position of the person's body, which can be represented by a line connecting the person's head and the torso, can take on any angle between 0 and 360 degrees within a video frame that captures the person's body. In some embodiments, to train pose-estimation module 106 so that the trained pose-estimation module 106 can recognize different scenarios/poses of a person's fall corresponding to the different possible angles of the person being captured in a video frame, a training image set can be prepared to include images of falls that simulate various capturing angles between 0 and 360 degrees. The training image set can then be used to train pose-estimation module 106 to improve the pose estimation performance for different imaging capturing angles.

After making the above modifications/improvements to the existing bottom-up pose-estimation technique and implementing the modified network in pose-estimation module 106, it is observed that the inference speed of the proposed pose-estimation technique implemented on a Hi3559A-based embedded platform can be reduced from ~550 ms to ~86 ms when processing an input image size of 656×368 pixels.

In some embodiments, after locating human keypoints 122 of a detected person in an input video image 104, the full image of the detected person can be cropped out from input video image 104 by forming a bounding box around the set of keypoints 122 and the associated skeleton representation of the detected person.

Action-Recognition Module

Referring back to FIG. 1, note that pose-estimation module 106 is coupled to action-recognition module 108, which is configured to receive the outputs from the pose estimation module. In some embodiments, the outputs from pose-estimation module 106 can include detected human keypoints 122, the associated skeleton diagram (also referred to as the "stick figure diagram" throughout), and a two-dimensional (2-D) image 132 of the detected person cropped out from original video image 104 based on the detected keypoints 122 (also referred to as "cropped image 132" of the detected person). Action-recognition module 108 is further configured to predict, based on the outputs from pose-estimation module 106, what type of action or activity the detected person is associated with. For example, action-recognition module 108 can include an action classifier 128 configured to classify each detected person as being in one of a set of pre-defined actions, referring to as action label/ classification 124 for the detected person. In some embodiments, action classifier 128 can be configured to use only cropped image 132 of the detected person to classify the action for the detected person. In some other embodiments, action classifier 128 can be configured to use only the human keypoints 122 of the detected person to classify the action for the detected person. Note that using cropped image 132 to classify the action for the detected person typically can achieve more accurate results than using only human keypoints 122 to classify the action for the detected person. In still other embodiments, action classifier 128 can be configured to use the combined data of cropped image 132 and human keypoints 122 of the detected person to classify the action for the detected person.

More specifically, cropped image 132 of the detected person and/or the set of human keypoints 122 of the detected person can be fed into action classifier 128 configured to predict the probability of the detected person being in a given action among a set of pre-defined actions related to the person's state of daily living, and subsequently classify the detected person to one of these pre-defined actions based on the set of probabilities corresponding to the set of pre-defined actions. For example, for fall-monitoring and fall-detection applications, an exemplary set of pre-defined actions of interests can include the following five actions: (1) standing; (2) sitting; (3) bending; (4) struggling; and (5) lying down. In some embodiments, a CNN-based architecture can be used to construct such an action classifier. Note that among these five pre-defined actions, the first three actions are generally considered as normal actions, whereas the last two actions are generally considered as dangerous actions indicative of a fall. In some embodiments, to perform this action classification in action-recognition module 108, 5 classes of data are collected based on the above-described 5 types of actions, which can then be used to train a neural network to classify the 5 types of actions.

Figure 4:
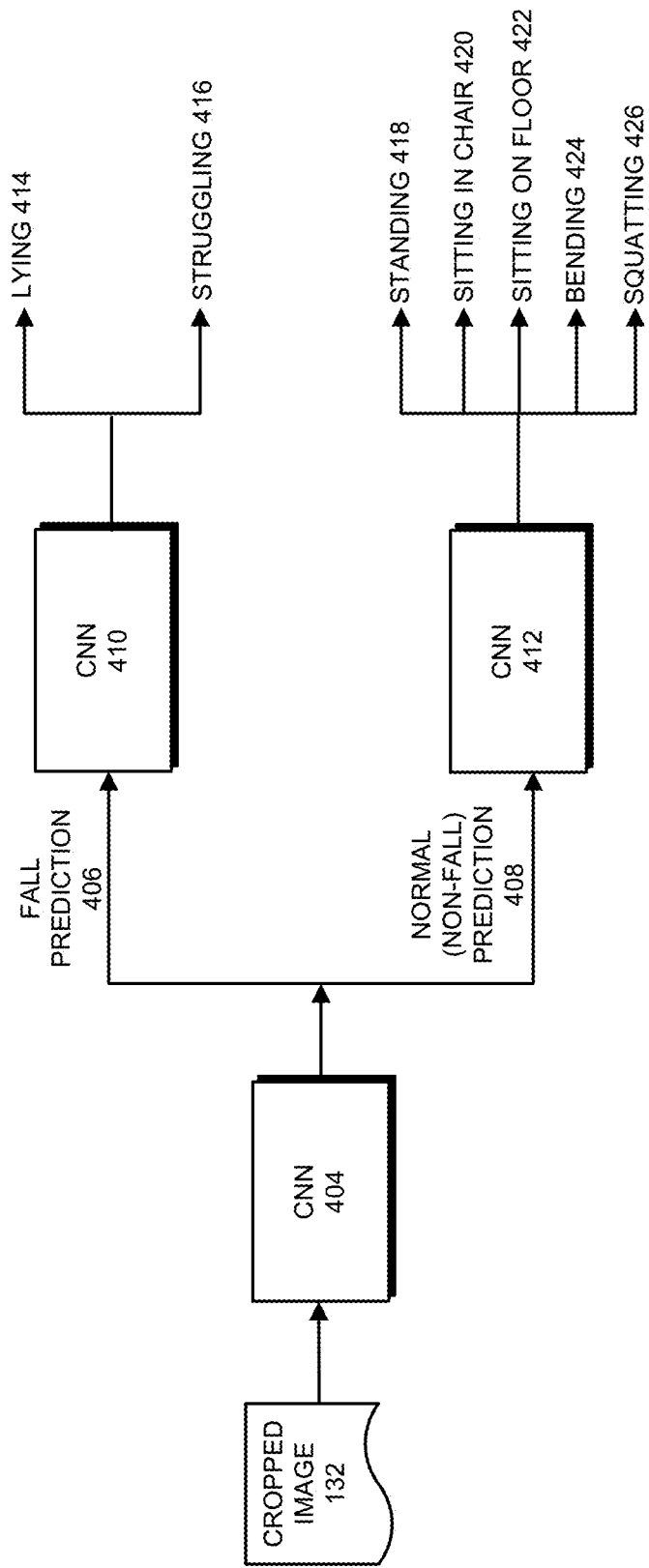
FIG. 4 shows a block diagram illustrating an exemplary two-level action-recognition module for classifying actions based on cropped images of a detected person in accordance with some embodiments described herein.

In some embodiments, to improve prediction accuracy, action classifier 128 can be configured to implement a two-level action recognition technique based on using CNN architectures. FIG. 4 shows a block diagram illustrating an exemplary two-level action-recognition module 400 for classifying actions based on cropped images of the detected person in accordance with some embodiments described herein. However, as mentioned above, other embodiments of the disclosed action-recognition module can also use the human keypoints 122 instead of cropped image 132, or the combination of cropped image 132 and human keypoints 122 as inputs to the action classifiers.

As can be seen in FIG. 4, in the first level of action recognition, a first CNN module 404 receives a cropped image 132 and uses a binary classifier (not shown) to generate a "fall" prediction 406 and a "normal" (i.e., non-fall) prediction 408 for the detected person in input image 132. Note that each of the fall prediction 406 and normal prediction 408 is associated with a category of different actions. Next, in the second level of action-recognition module 400, two more CNNs 410 and 412 are employed and configured to further characterize each of the binary predictions 406 and 408 into a more specific action in the associated category of actions.

More specifically, CNN 410 can further classify a fall prediction 406 into a set of actions related to a fall. In the embodiment shown in FIG. 4, these fall actions can include a "lying" action 414 and a "struggling" action 416. However, other embodiments of action-recognition module 400 can include additional actions or a different set of fall actions as the possible outputs of CNN 410. Separately, CNN 412 can further classify a normal prediction 408 into a set of actions related to a non-fall condition. In the embodiment shown in FIG. 4, these normal actions can include a "standing" action 418, a "sitting in chair" action 420, a "sitting on floor" action 422, a "bending" action 424, and a "squatting" action 426. However, other embodiments of action-recognition module 400 can include additional actions or a different set of non-fall actions as the possible outputs of CNN 412.

Note that either in the disclosed single-level action-recognition technique or the two-level action-recognition technique of FIG. 4, various fast CNN architectures can be used to classify the actions of people detected by the embedded vision system. In one embodiment, a SqueezeNet architecture (described in "*SqueezeNet: AlexNet-level accuracy with 50× fewer parameters and <0.5 MB model size,*" Iandola, arXiv:1602.07360, 2016) can be used. In some embodiments, to implement the SqueezeNet architecture in the disclosed action-recognition module 108, one can modify the number of output classes in the existing CNN networks based on the number of pre-defined actions/activities to be detected while retraining the configurations of the neural networks.

For example, in the above-described single-level action-recognition technique including 5 classes of actions, the number of output classes in the SqueezeNet network can be reduced to 5 while retraining the same neural network configuration. However, to implement the disclosed action-recognition techniques for detecting greater or fewer numbers of actions of interest, one can easily modify the SqueezeNet network with more or less output classes.

Note that the disclosed action-recognition techniques implemented on action-recognition module 108 are generally applied to individual video frames to generate an action classification for each detected person in each processed video frame. Meanwhile, the disclosed action-recognition techniques can be continuously applied to a sequence of video frames on a frame-by-frame basis, and can continue to generate updated action classifications for each detected person based on the newly processed frames. Hence, in some embodiments, the disclosed action recognition techniques may be referred to as frame-level action-recognition techniques, while action-recognition module 108 may be referred to as frame-level action-recognition module 108.

Scene-Segmentation Module

In some embodiments, to robustly and reliably detect a fall action, especially falling from a bed or a sofa, the disclosed embedded fall-detection system 100 is configured to distinguish different types of lying and struggling actions of a detected person. For example, lying in bed or sofa would generally be classified as normal human actions (i.e., non-fall actions), whereas lying or struggling on the floor would be classified as dangerous actions (i.e., fall actions). In some embodiments, the ability to distinguish different types of lying and struggling actions of a detected person can be achieved by scene-segmentation module 112, which is configured to process input video images 104 and extract room layout information 126.

More specifically, room layout information 126 can include locations of dangerous regions/objects such as a floor and a carpet. In some embodiments, if an identified lying action of the detected person is determined to be within an identified dangerous region, such as a floor region, it is reasonable to classify an identified lying action as a dangerous action (e.g., falling on the floor). Moreover, if the identified lying action was previously classified as a dangerous action by action-recognition module 108, such classification can be further confirmed by the room layout information 126, e.g., by increasing the probability/confident score of the classification. Room layout information 126 can also include locations of normal regions/objects such as a bed and a sofa. In some embodiments, if an identified lying action of the detected person is determined to be within an identified normal region, such as a bed, it is reasonable to classify the identified lying action as a normal action (e.g., sleeping on the bed). Moreover, if the identified lying action was previously classified as a normal action, such classification needs to be reclassified as a dangerous action based on room layout information 126. Note that because room layout information 126 is relatively static, scene-segmentation module 112 does not have to extract room layout information 126 from every input video frame 104. In some embodiments, scene-segmentation module 112 only extracts room layout information 126 periodically, e.g., for every N input video frames 104 (wherein N is determined based on a predefined time period). In some embodiments, room layout information 126 can also be extracted during the setup/installation/initialization of distributed fall-detection system 200, or when requested by the user of the distributed fall-detection system 200 through a button within mobile app 212 from a mobile device.

In some embodiments, scene-segmentation module 112 can be implemented by various fast CNN-based semantic segmentation models. In one embodiment, scene-segmentation module 112 can be implemented based on a Deep-LabV3+ model (described in "*Encoder-Decoder with Atrous Separable Convolution for Semantic Image Segmentation*," arXiv:1802.02611, Chen et al., August 2018), which can achieve good scene segmentation performance by combining the advantages of both a spatial pyramid pooling technique and an encode-decoder structure. In some embodiments, scene-segmentation module 112 can be implemented based on the DeepLabV3+ model by making some or all of the following modifications/improvements to the original DeepLabV3+ model:

Modifying the original DeepLabV3+ network output to segment the indoor scenes into three regions/categories: (1) the dangerous region which can contain the floor and a carpet; (2) the safe region which can contain objects where one can lie down, such as a bed and a sofa; and (3) the background region such as walls and furnitures other than bed and sofa;

Modifying the original DeepLabV3+ model by using a fast MobileNetV2 network (described in "*MobileNetV2: Inverted Residuals and Linear Bottlenecks*," Sandler et al., arXiv:1801.04381) as the backbone/feature extractor the modified DeepLabV3+ model to speed up and simplify the original DeepLabV3+ model. Note that the MobileNetV2 network is based on depth-wise convolution, wherein a high-dimensional tensor is approximated by the product of low-dimensional tensors. However, other networks similar to MobileNetV2 network can be used in place of MobileNetV2 network as the backbone in the above-described modification to the original Deep-LabV3+ network;

Quantizing the network parameters and running the network inference in 8-bit integer precision instead of the existing 32-bit floating-point precision to reduce the memory usage and the frequency of memory access, and to speed up the arithmetic computations, thereby making the modification particularly useful and desirable in resource-limited embedded system applications; and Removing some preprocessing functions embedded in the original DeepLabV3+ model and implementing these functions on a CPU.

The above-described network modifications/improvements can significantly speed up the execution of the disclosed scene-segmentation model. For example, the runtime of the disclosed scene segmentation model on Hi3559A CPU can be reduced from about 43 seconds to ~2 seconds when the above modifications are implemented. In some embodiments, the disclosed scene-segmentation module 112 is only executed during the booting-up phase of embedded fall-detection system 100 or distributed fall-detection system 200 when the system is being calibrated, or when there is no motion in the input video images 104 for some time. As a result, the execution speed of the disclosed scene-segmentation module 112 is sufficient fast to allow room layout information 126 to be generated for an input image before the generation of action labels 124 for that input image.

Fall-Detection Module

Referring back for FIG. 1, note that action-recognition module 108 is followed by fall-detection module 110, which receives the outputs from both pose-estimation module 106 (i.e., human keypoints 122) and action-recognition module 108 (i.e., the action labels/classifications 124). As described above, embedded fall-detection system 100 uses pose-estimation module 106 to identify human keypoints 122 of each detected person, estimate the locations of human keypoints 122 in the corresponding video frame 104, and output cropped image 132 of each detected person based on the human keypoints 122. Action-recognition module 108 can then use cropped image 132 and/or keypoints 122 of a detected person to generate frame-by-frame action labels/classifications 124 for the detected person. Subsequently, fall-detection module 110 can use at least the action labels/classifications 124 from action-recognition module 108 to distinguish dangerous actions from normal actions, and subsequently generate fall-detection output 140 including both a fall alarm 140-1 and a corresponding sanitized video clip 140-2 if a fall of the detected person can be confirmed.

However, to generate more reliable fall-detection output 140, a room layout and temporal information of a sequence of video frames need to be considered. As described above, scene-segmentation module 112 is configured to provide the room layout information 126 relevant to the fall detection. As shown in FIG. 1, scene-segmentation module 112 can receive raw video images 104 and process video images 104 in parallel to the processing of video images 104 by pose-estimation module 106 and action-recognition module 108. Hence, scene-segmentation module 112 can identify certain room layout information from each video image 104, which can includes, but not limited to the floor, the bed, and the sofa in the input video frame. Note that fall-detection module 110 can receive room layout information 126 from scene-segmentation module 112 and combine this information with received human keypoints 122 from pose-estimation module 106 and action labels 124 from action-recognition module 108 when making fall-detection decisions.

As can be seen in FIG. 1, fall-detection module 110 can additionally include a state machine 120 and an invalid pose filter 138. By combining room layout information 126 from scene-segmentation module 112 with the functionalities of the later described state machine 120 and invalid pose filter 138, fall-detection module 110 can generate highly-reliable fall-detection output 140. We now describe scene-segmentation module 112, state machine 120, and invalid pose filter 138 in more details below.

Fall-Detection State Machine

Figure 5:
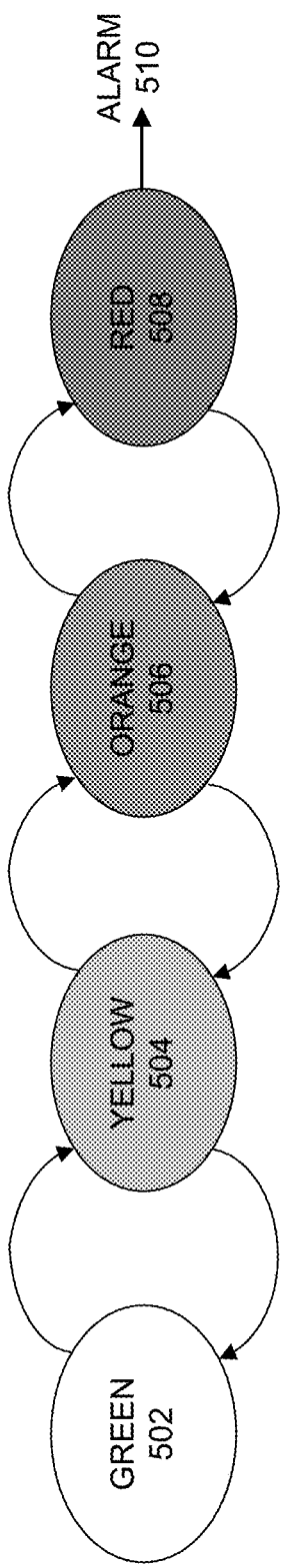
FIG. 5 shows fall-detection state transition diagram of the disclosed state machine for predicting falls based on a set of consecutive action labels of a detected person in accordance with some embodiments described herein.

Note that if fall-detection module 110 generates fall alarms/notifications 140-1 directly based on frame-by-frame action labels/classifications 124 generated by action-recognition module 108, then fall alarms/notifications 140-1 can include false alarms because such fall decisions generally do not take into account correlations among consecutive video frames and the continuous nature of a given human action. In some embodiments, to reduce false alarms caused by the more naive frame-by-frame action recognition/fall-detection technique, a state machine 120 can be developed which incorporates temporal information from consecutive video frames into fall-detection decisions by fall-detection module 110. An exemplary implementation of state machine 120 is shown in FIG. 5. By combining the outputs from action-recognition module 108 and the temporal correlations between consecutive video frames using the disclosed state machine 120, the fall/non-fall decisions generated by fall-detection module 110 become more robust and reliable and fall alarms generated by fall-detection module 110 can include significantly less false alarms.

FIG. 5 shows a fall-detection state transition diagram 500 of the disclosed state machine 120 for predicting falls based on a set of consecutive action labels of a detected person in accordance with some embodiments described herein. As can be seen in FIG. 5, the disclosed state transition diagram 500 can include four states representing different levels of fall possibility: "green" state 502, "yellow" state 504, "orange" state 506 and "red" state 508. More specifically, green state 502 represents the normal state associated with normal actions/activities of the detected person, yellow and orange states 504-506 represent the warning states associated with potentially risky actions/activities of the detected person, and red state 508 represents the alarm state associated with dangerous actions/activities of the detected person indicative of a fall.

In some embodiments, each of the states 502-508 in state transition diagram 500 is associated with a state score, and a pre-specified upper bound and a pre-specified lower bound associated with the state score. Hence, each time the state score of the current state of the state machine is updated, the updated state score can be compared to the pre-specified upper/lower bounds. If the updated state score is going above/below the upper/lower bounds of the current state, the state of state transition diagram 500 will transition to a more/less dangerous state in the set of states 502-508, as shown in state transition diagram 500 with the arrows between these states. Moreover, a fall alarm 510 (and hence a fall alarm 140-1 in FIG. 1) can be generated when the alarm state (i.e., red state 508) is reached, which indicates that a fall has occurred.

In some embodiments, each state in state transition diagram 500 can have a maximum state score of 100 (i.e., the upper bound) and a minimum state score of 0 (i.e., the lower bound). The recognized dangerous actions by action-recognition module 108 (e.g., struggling and lying on the floor) can be used to increase the state score associated with a current state, whereas the detected normal actions (e.g., standing, sitting, bending, and squatting) can be used to decrease the state score associated with a current state. Consequently, for a sequence of video frames depicting a continuous human action of a detected person, the state score of the current state can be continuously increased or decreased. Note that, as long as the current state score is bounded between the associated upper bound and the lower bound, the current state in the fall-detection state transition diagram 500 does not transition to another state.

However, when the current state score exceeds the associated upper bound, the current state will transition to a more dangerous state in state transition diagram 500, for example, from orange state 506 to red state 508, thereby triggering a fall alarm 510. On the other hand, when the current state score goes below the associated lower bound, the current state will transition to a less dangerous state, e.g., from yellow state 504 to green state 502. Note that while different color-coded states in state transition diagram 500 represent different severities of the current state of a detected person in terms of the risk of falling, these states are generally not corresponding to specific actions of the person, such as standing, sitting, bending, or lying. Note that while the embodiment of state transition diagram 500 includes four states, other embodiments of state machine 120 can include a greater or fewer number of states. For example, one embodiment of state machine 120 can include only three states with just one warning state instead of the two warning states as shown in FIG. 5.

We now describe an exemplary technique for determining the state score for the current state of state transition diagram 500. Recall that human keypoints 122 generated by pose-estimation module 106 are part of inputs to fall-detection module 110. As described above, when generating human keypoints 122 for a detected person, pose-estimation module 106 can also generate a probability for each keypoint 122. Hence, for the detected person, we can first calculate two types of weighted scores $w_{fall}$ and $w_{normal}$ for the person from the set of detected keypoints 122 of that person, wherein $w_{fall}$ are calculated for fall actions and $w_{normal}$ are calculated for normal actions. For example, the weighted scores $w_{fall}$ and $w_{normal}$ can be defined as:

$$w_{fall} = W_k \cdot (P_k \otimes W_{floor}); \quad (1)$$

$$w_{normal} = -W_k \cdot P_k, \quad (2)$$

In Eqn. (1) above, "$\otimes$" denotes the element-wise product of two vectors, and "$\bullet$" denotes the dot product of two vectors. Assuming that the detected person is in the dangerous region (i.e. floor region), $w_{fall}$ will have a positive value, while $w_{normal}$ will have a negative value. For example, if the detected person is lying on the floor which is considered to be a dangerous region, both $W_{floor}$ and $w_{fall}$ will be positive, which will also cause the state score described in Eqn. (3) below to increase. However, when the detected person is in the normal/safe region, $w_{fall}$ will have a negative value because elements in $W_{floor}$ will be set to all negative values, while $w_{normal}$ will also have a negative value. For example, if the detected person is lying in bed which is considered to be a normal region, both $w_{fall}$ and $W_{floor}$ will be negative, which will cause the state score described in Eqn. (3) below to decrease. Note that regardless whether the detected person is in a dangerous region or a normal region, $w_{normal}$ remains negative because it is always associated with normal situations.

For the exemplary skeleton diagram/representation of a detected person shown in FIG. 3, $P_k$ can be an 18×1 keypoint probability vector formed by the probabilities of the 18 keypoints of the estimated pose, and $W_k$ is an 18×1 keypoint weight vector formed by 18 weight values associated with the 18 keypoints of the estimated pose. In some embodiments, to facilitate detecting falls, larger weight values in $W_k$ can be assigned to lower limb keypoints whereas smaller weight values in $W_k$ can be assigned to upper body keypoints. Moreover, because a fall action is strongly correlated to whether the detected person is in a dangerous region (e.g., the floor area), we can integrate the extracted floor information by room layout information 126 into the first type of weighted score $w_{fall}$ through vector $W_{floor}$. For example, in the same 18 keypoints example of FIG. 3, $W_{floor}$ can be configured as an 18×1 mask vector. In some embodiments, when a keypoint of the detected person is determined to be in the dangerous region (e.g., on or near the floor or carpet), the corresponding weight element in $W_{floor}$ can be set to 1 so that this keypoint will have a positive contribution to the fall action, and subsequently a positive contribution to the state score described below. Otherwise (i.e., when the keypoint is not in the dangerous region), the value of the corresponding weight element in $W_{floor}$ is set to −1 so that this keypoint will have a negative contribution to the fall action, and subsequently a negative contribution to the state score described below. Generally speaking, $w_{normal}$ is designed to be a negative value which has little or no correlation to the floor information. Consequently, when a normal action is detected, a corresponding $w_{normal}$ can be computed based on Eqn. (2), which will have a negative contribution to the state score described below.

As mentioned above, each state in the state transition diagram 500 can maintain a state score. In some embodiments, the state score s for the current state in the state transition diagram 500 can be updated based on the following equation:

$$s = s' + w_s \bullet (W_a \otimes P_a), \quad (3)$$

wherein s and s' are the state scores in the current and previous video frames, respectively, and $w_s = [w_{fall}, w_{normal}]^T$ is the vector form of the above-described weighted scores $w_{fall}$ and $w_{normal}$ of the detected person in the current video frame. Moreover, $P_a$ is a 2×1 vector including two probabilities associated with the "fall action" and "normal action" predictions from the first-level output of action-recognition module 108, $W_a$ is a 2×1 positive weighting vector including two weight values associated with the two categories of actions (i.e., fall actions and normal actions), respectively, and $W_a \otimes P_a$ is the dot product of the these two vectors. Assuming that the detected person is in the dangerous region (i.e. floor region), $w_{fall}$ will have a positive value, while $w_{normal}$ will have a negative value. Subsequently, each identified dangerous action of the detected person will cause the current state score s to increase toward the upper bound of the current state; whereas each identified normal action of the detected person will cause the current state score s to decrease toward the lower bound of the current state. By way of example, a typical example of $P_a$ associated with a possible fall action can be $P_a = [0.9, 0.1]^T$. In this case, based on Eqns. (1)-(3), a positive value will be added to s', which will cause current state score s to increase. On the other hand, a typical example of $P_a$ associated with a possible normal action can be $P_a = [0.9, 0.1]^T$. In this case, based on Eqns. (1)-(3), a negative value will be added to s', which will cause current state score s to decrease.

Generally speaking, by tuning the values of the two elements in $W_a$, one can modify the sensitivity and robustness of the disclosed state machine. More specifically, the two elements of $W_a$ are corresponding to the fall and normal actions, respectively, wherein one of the two elements (e.g., the first element) of $W_a$ can be used to control how long it will take for a fall action to trigger an alarm, and the other element (e.g., the second element) of $W_a$ can be used to control how long it will take for a normal action to recover from a fall alarm back to green state 502. Hence, by properly setting the value of the element in $W_a$ associated with fall actions, it is possible to tune the disclosed state machine to be more or less sensitive to fall actions. By way of example, to avoid certain false alarms in fall detection, we can set $W_a [10, 30]^T$ so that a normal action controlled by the second element can have a stronger effect on the state score s. Using this setup, if 50% of the input video frames within a predetermined period of time are classified as being associated with fall actions, the fall alarm would not be triggered. Instead, it may require approximately 75% of the input frames within the predetermined period of time to be classified as fall actions to trigger the fall alarm. Based on this setup, embedded fall-detection system 100 can have an increased confidence level in fall-detection output 140. In this manner, the disclosed $W_a$ can control the confidence level in fall detections by tuning the sensitivity to fall actions.

In some embodiments, when a person is first detected by embedded fall-detection system 100 in an input video image 104, an initial state score $s_0$ can be assigned to this person. In some embodiments, it can be assumed that the detected person is initially in a perfectly normal condition so that the initial state of the person can be set to the normal state in the state transition diagram, which is the green state 502 in the exemplary state transition diagram 500, and the initial state score $s_0$ can be set to the lower bound of the normal state. However, in other embodiments, the initial state score $s_0$ can have set to a value in the middle between the upper bound and the lower bound of the normal state.

Invalid Pose Filter

Note that when a person is standing too close to camera 102 of embedded fall-detection system 100, the lower limbs of the person may be cut off by the field of view of the camera, and action-recognition module 108 is likely to misclassify the standing action as a struggling or lying action. In some embodiments, to filter out these false alarms, fall-detection module 110 can additionally include an invalid pose filter 138 which can be used to check for invalid pose locations, and the associated keypoints and skeleton segments. More specifically, we can define a set of binary flags corresponding to a set of invalid poses. For example, the set of binary flags can include three flags $f_c$, $f_{pt}^i$ (i=1 to 18), $f_l^j$ (j=1 to 17) defined as follows:

Invalid pose flag: $f_c$ is set to 1 if the coordinates of the center of the detected pose in an input video image is below a certain threshold (e.g., when the center of the pose is too low in the video image). Otherwise, $f_c$ can be set to 0;

Invalid keypoints flag: $f_{pt}^i$ is set to 1 if the i-th keypoint in the detected pose in an input video image is missing, e.g., when the i-th keypoint is out of the field of view. Otherwise, $f_{pt}^i$ can be set to 0;

Invalid skeleton segments flag: $f_l^j$ is set to 1 if the length of the j-th skeleton segment in the detected pose in an input video image exceeds a predetermined threshold value. Otherwise $f_l^j$ can be set to 0. For example, when a person is standing too close to camera 102, the lengths of certain skeleton segments, such as eye-ear segment, eye-nose segment, and/or nose-chest segment can be significantly larger than normal values, and can also exceed the corresponding threshold values.

The above-defined flags can then be fused/combined into a weighted invalidity score $s_{inv}$ as follows:

$$s_{inv} = w_c \times f_c + w_{pt} \Sigma_{i=1}^{18} f_{pt}^i + w_l \Sigma_{j=1}^{17} f_l^j, \quad (3)$$

wherein $w_c$, $w_{pt}$, $w_l$ are the weights assigned to the center of the pose, keypoints and skeleton segments, respectively. In some embodiments, if the computed invalidity score $s_{inv}$ is larger than a predetermined threshold, the detected pose by action-recognition module 108 can be marked as invalid and is ignored by embedded fall-detection system 100. As a specific example of using this filter, we can assign a larger value to $w_l$ to more effectively filter out false alarms caused by standing skeleton representations of people positioned too close to the camera.

Note that when the disclosed embedded fall-detection vision sensors are installed in hallways, the cameras are usually mounted higher than in the rooms in order to cover larger areas. For these hallway applications, a rectangle invalid zone can be set up at the bottom of the screen/field-of-view to filter out skeleton representations of people detected in the rectangle invalid zone, i.e., at the bottom of the screen. In some embodiments, multiple embedded fall-detection vision sensors 202-1, 202-2, . . . , and 202-N can be set up in such a way so that each invalid zone of each standalone embedded vision sensor 202-i (i=1 to N) can be covered by one or more of the neighboring embedded vision sensors 202. In some embodiments, the size of the invalid zone of an installed embedded vision sensor 202-i can be determined based on the height of the embedded vision sensor 202-i from the floor.

Figure 6:
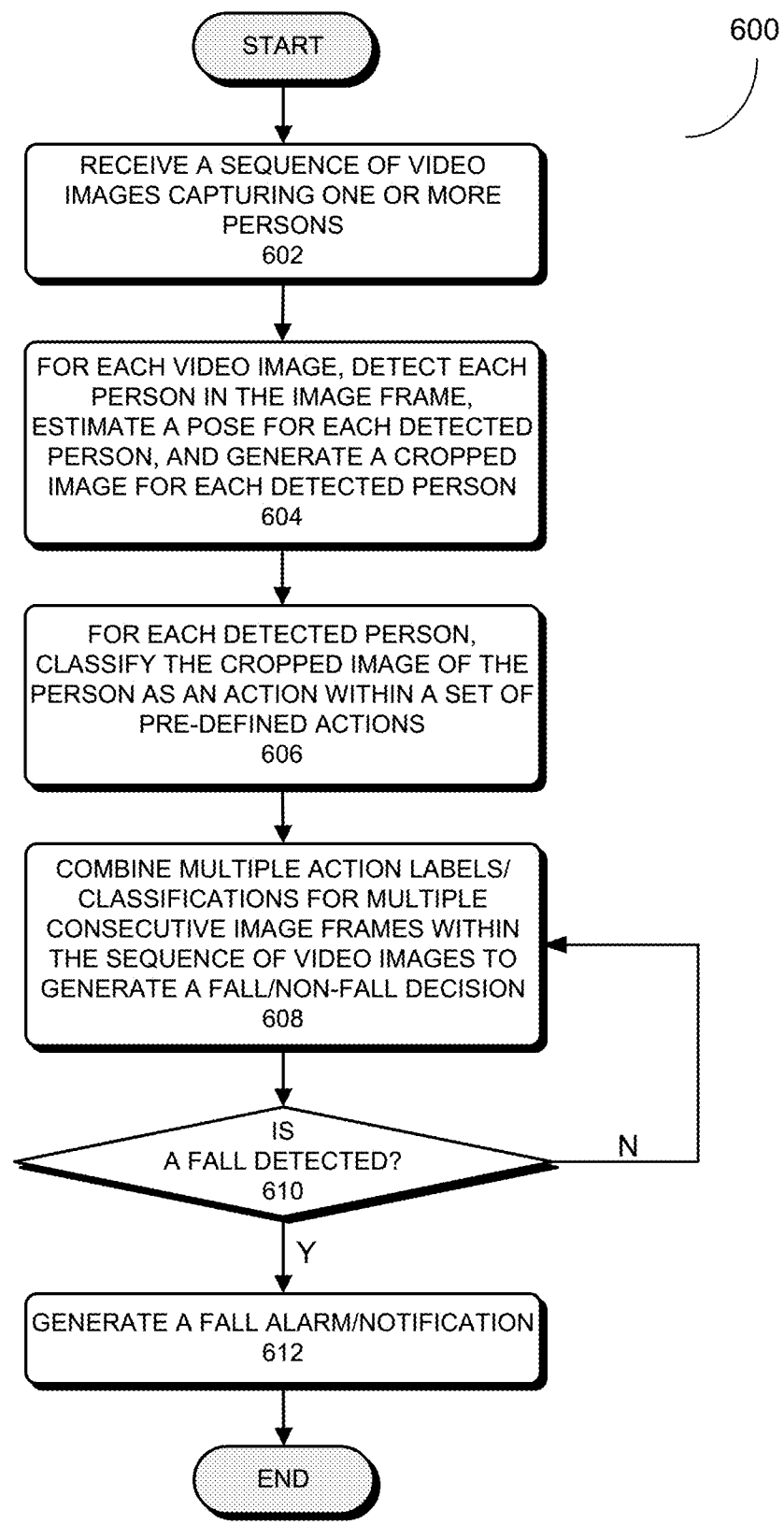
FIG. 6 presents a flowchart illustrating an exemplary process for performing image-based fall detection in accordance with some embodiments described herein.

FIG. 6 presents a flowchart illustrating an exemplary process 600 for performing image-based fall detection in accordance with some embodiments described herein. In one or more embodiments, one or more of the steps in FIG. 6 may be omitted, repeated, and/or performed in a different order. Accordingly, the specific arrangement of steps shown in FIG. 6 should not be construed as limiting the scope of the technique.

Process 600 may begin by receiving a sequence of video images capturing one or more persons being monitored for potential falls (step 602). For example, the video images may be captured by a fall-detection camera installed at an assisted living facility or a nursing care home, and the one or more persons being monitored can be elderly people living in the assisted living facility or the nursing care home. In the captured images, the one or more persons can be performing any activities of daily living (ADLs), such as sleeping, sitting, walking, and other types of ADLs. Next, for a given video image in the sequence of video images, process 600 detects each person in the video image, and subsequently estimates a pose for each detected person and generates a cropped image for the detected person (step 604). For example, process 600 can first identify a set of human keypoints for each detected person and then generate a skeleton diagram/stick figure of the detected person by connecting neighboring keypoints with straight lines. In various embodiments, step 604 can be performed by the disclosed pose-estimation module 106 of embedded fall-detection system 100.

Next, for each detected person, process 600 classifies the cropped image of the detected person as a particular action within a set of pre-defined actions, such as (1) standing; (2) sitting; (3) bending; (4) struggling; and (5) lying down (step 606). In some embodiments, process 600 can employ the aforementioned two-level action-recognition technique described in conjunction with FIG. 4 to classify the action in the cropped image by: (1) classifying the action as either a general "fall" action or a general "non-fall/normal" action; and (2) further classifying the classified general action into a specific action within a category of actions associated with the classified general action. In various embodiments, step 606 can be performed by the disclosed action-recognition module 108 of embedded fall-detection system 100.

Next, for each detected person, process 600 combines multiple action labels/classifications generated for multiple consecutive video images within the sequence of video images to generate a fall/non-fall decision (step 608). As mentioned above, by combining the action classifications generated for the multiple consecutive video images, process 600 takes into account the correlations among the consecutive video frames including the temporal correlations, and subsequently makes fall/non-fall decisions with higher reliability by reducing or eliminating false alarms typically associated with frame-by-frame based fall-detection decisions. In some embodiments, step 608 can be performed by the state machine 120 of fall-detection module 110 within embedded fall-detection system 100. Note that, to further increase the reliability of the fall/non-fall decisions, room layout information such as the locations of the floor, the bed, and the sofa can be extracted from the multiple consecutive video images and combined with other inputs to action classifiers of fall-detection module 110 to further distinguish different types of lying and struggling actions of each detected person. In various embodiments, such room layout information can be generated by scene-segmentation module 112 of embedded fall-detection system 100.

Process 600 next determines if a fall has been detected based on the fall/non-fall decision (step 610). For example, using state transition diagram 500, step 610 determines that, after processing the multiple consecutive video images, whether the current state of the system is in red state 508 of state transition diagram 500 or not. If so, process 600 generates a fall alarm/notification (step 612). Otherwise, process 600 can return to step 608 to use the most recent action labels/classifications to update the fall/non-fall decision and continue the fall monitoring/detection process.

Infrared Image-Based Detection of Falling from Bed

In some embodiments, the embedded fall-detection system 100 can also be configured to detect a falling-off-bed event/action, e.g., when a monitored person lying on the bed is experiencing a serious medical condition that would result in a fall from the bed to the floor. In particular, to detect such falls in a dark environment, e.g., at night, a visual sensor such as a camera with a night vision mode/function can be used. Specifically, when the lighting condition within a monitored area is poor, e.g., when the level of illumination is determined to be below a detection threshold, embedded fall-detection system 100 can automatically turn on an infrared (IR) lighting/light source and, if necessary, also turn off the IR filter to begin capturing infrared video/images. The captured infrared images can then be transformed into grayscale images, which can then be used as inputs to pose-estimation module 106, action-recognition module 108, fall-detection module 110, and scene-segmentation module 112 for fall detections.

In some embodiments, embedded fall-detection system 100 can be configured to process both daylight RGB input images and night-vision infrared input images. Moreover, embedded fall-detection system 100 can also be configured to handle special requirements for falling-off-bed detection. For example, even when a person being monitored is covered by a blanket or a comforter, pose-estimation module 106 can still detect the head and shoulder keypoints of the person which generally remain visible, and subsequently estimate the positions of the upper body and limb keypoints for the person. Action-recognition module 108 can then be used to generate the proper action labels for the detected person based on the cropped images of the person and/or the skeleton representations of the person, and subsequently trigger the fall-detection state machine 120 within fall-detection module 110 to transition accordingly.

Statistics of Activities of Daily Living (ADLs)

In some embodiments, embedded fall-detection system 100 can also be used to recognize and generate statistics of a person's activities of daily living, e.g., how much time is spent on sleeping, sitting, and moving. More specifically, outputs of scene-segmentation module 112 and outputs of action-recognition module 108 based on analyzing consecutive video frames can be combined to recognize various activities of daily living (ADLs), such as sleeping and walking. Based on this ADL information, useful statistics can be generated for a monitored person, such as how much time of the person is spent on sleeping, sitting, walking, and other types of ADLs. In some embodiments, embedded fall-detection system 100 can periodically output the generated ADL statistics of a monitored person, e.g., as a part of fall-detection output 140. By merging such ADL statistics from multiple embedded fall-detection vision sensors installed within a healthcare facility or a house, the disclosed distributed fall-detection system 200 can obtain the ADL summary of each person being monitored, and such summary can be used by caregivers to analyze the person's health condition. In some embodiments, embedded fall-detection system 100 can include a dedicated ADL statistics module (not shown) for computing the above ADL statistics.

Face Detection and Face Recognition Modules

Referring back to FIG. 1, note that embedded fall-detection system 100 also includes face-detection module 116 configured to perform face detection functions. Specifically, face-detection module 116 can directly receive raw video images 104 and process video images 104 in parallel to the processing of video images 104 by pose-estimation module 106, action-recognition module 108, and scene-segmentation module 112. Face-detection module 116 subsequently outputs detected face 130 within video images 104.

There are many fast face-detection models which can be used to implement face-detection module 116 in embedded fall-detection system 100. In one embodiment, a S3FD model (described in "*S3FD: Single Shot Scale-invariant Face Detector,*" Zhang et al., ICCV 2017) can be used to implement face-detection module 116. The S3FD model has shown to have good performances in handling faces of different scales. In some embodiments, to run a S3FD-based face detect model in real-time on embedded fall-detection system 100, the following modifications/improvements can be made to the original S3FD model:

Replacing the complex VGG16 network in the original S3FD model with a lightweight MobileNetV2 (described in "*MobileNetV2: Inverted Residuals and Linear Bottlenecks,*" Sandler et al., arXiv:1801.04381) as the backbone/feature extractor;

Incorporating the feature pyramid network (FPN) (described in "*Feature Pyramid Networks for Object Detection,*" Lin et al., arXiv:1612.03144, 2016) into the modified S3FD framework to improve the small faces detection performance;

Reducing the training and inference data size in the original S3FD model design from 640×640 to 320×320 to further reduce the inference speed;

Adding a landmark-detection CNN module which is configured to receive face detection outputs from the modified S3FD network and output accurate facial landmarks for the detected faces for use in subsequent face recognition operation. In some embodiments, the landmark-detection CNN module and the S3FD-based face detection model can be jointly trained; and Quantizing the network parameters and running the network inference in 8-bit integer precision instead of in the existing 32-bit floating-point precision to reduce the memory usage and the frequency of memory access, and to speed up the arithmetic computations, thereby making the modification particularly useful and desirable in resource-limited embedded system applications.

Based on the above-described modifications, the disclosed S3FD-based face detection model can reduce the face-detection inference time from ~1.2 s to ~100 ms on an ARM v8 CPU. Note that this performance improvement can be achieved without using any neural network acceleration engine.

Further referring to FIG. 1, note that the disclosed embedded fall-detection system 100 also includes face-recognition module 118 configured to perform face recognition functions based on the detected faces 130 from face-detection module 116. There are many good face recognition models which can be used to implement face-recognition module 118 in embedded fall-detection system 100. In one embodiment, an ArcFace face recognition model (described in "*ArcFace: Additive Angular Margin Loss for Deep Face Recognition,*" Deng et al., arXiv:1801.07698, 2018) can be used to implement face-recognition module 118. In a particular implementation of face-recognition module 118, a number of modifications have been made to the original ArcFace model to tailor to the needs of embedded fall-detection system 100. First, the proposed face-recognition model can train a lightweight ResNet-18 network (described in "*Deep Residual Learning for Image Recognition,*" He et al., CVPR 2016) on the MS1M-refine-v2 dataset. Second, the proposed face-recognition model can be configured to quantize the neural network model and run the inference using 8-bit integer precision instead of 32-bit floating-point precision as in the original ArcFace model. With these modifications, the inference speed of the proposed face-recognition model can be reduced to about 12 ms on the Hi3559A NNIE engine. Note that using the above proposed implementation of the face-recognition module 118, it is also possible to detect other useful properties of people in the captured video images 104, such as facial expressions.

Person-ID Library and Profile Database

In some embodiments, during fall detection, face recognition module 118 can generate a facial feature vector (which can be a 1-D facial feature vector, a 2-D facial feature vector, or a 3-D facial feature vector) for each detected face within an input video image 104. Next, the generated facial feature vector can be compared against a person-ID dictionary, such as person-ID dictionary 150 stored in a memory of embedded fall-detection system 100. In some embodiments, the person-ID dictionary can include a set of entries associated with a set of existing/established person-IDs of a group of people that can be tracked by embedded fall-detection system 100, wherein each entry in the person-ID dictionary can include both one or multiple facial feature vectors (e.g., generated based on one or multiple profile photos, which can be 1-D facial feature vectors, 2-D facial feature vectors, or 3-D facial feature vectors) and a corresponding person-ID.

For each facial feature vector generated by face-recognition module 118 during the fall-detection process, if the facial feature vector matches a stored facial feature vector within an entry in the person-ID dictionary, it means that the detected person has an established profile at the server. Face-recognition module 118 will then output the person-ID within the matched entry as a person-ID 136 indicating that the detected person has been identified. In the same manner, face-recognition module 118 can output all person-IDs 136 for all of the detected persons that can be identified by face-recognition module 118 based on their corresponding facial feature vectors. Next, embedded fall-detection system 100 can output fall alarms 140-1 along with person-IDs 136 to the server, such as server 204. The server can then use a received person-ID 136 to locate the corresponding person's identity (e.g., the person's name) which has been previously established and stored on the server, and subsequently send a fall notification to the mobile app, such as mobile app 212 including the identity of the corresponding person which is determined to have fallen.

In some embodiments, the disclosed person-ID dictionary can be updated based on the following steps within distributed fall-detection system 200, which involve interactions among the one or multiple embedded vision sensors 202-1, 202-2, . . . , and 202-N, server 204, and mobile app 212:

Each user of distributed fall-detection system 200 can add or remove a person that is to be tracked by distributed fall-detection system 200 using mobile app 212. More specifically, for each person to be tracked by distributed fall-detection system 200, mobile app 212 can be used to construct a new profile of the person by combining the identity of the person with one or multiple profile photos of the person. For example, mobile app 212 can be used to take one or multiple profile photos of the person. Mobile app 212 can then send the profile of the person including the one or multiple profile photos and the person's identity, such as the name of the person to server 204;

Based on a received profile of a given person, server 204 can generate a unique person-ID (e.g., a unique integer value) for the given person, e.g., based on the identity of the person. Server 204 can then associate the unique person-ID with the received one or multiple profile photos of the given person. Server 204 then sends the unique person-ID along with the profile photos of the given person to the one or multiple embedded vision sensors 202-1, 202-2, . . . , and 202-N.

On each embedded vision sensor 202, the one or multiple profile photos of the given person can be used to extract one or multiple facial feature vectors for the person using the above-described face-detection module 116 and face-recognition module 118. Next, the person-ID dictionary, such as person-ID dictionary 150 can be updated by adding a new entry for the given person, wherein the new entry can store both the one or multiple newly generated facial feature vectors and the associated unique person-ID of the given person.

Next, during a fall-detection process, the person-ID dictionary can be used for person identification and tracking purposes on each embedded vision sensor 202. More specifically, face-recognition module 118 within each embedded vision sensor 202 can generate a facial feature vector for each detected person in an input image 104. Face-recognition module 118 can then search the generated facial feature vector of each detected person in the person-ID dictionary stored in a memory of each embedded vision sensor 202, and specifically compare the facial feature vector against the stored facial feature vectors in each entry of the person-ID dictionary. Recalled that each entry in the person-ID dictionary stores a profile of a known person, which can include one or multiple facial feature vectors, and a corresponding person-ID of the person. Based on the outcome of the search, face-recognition module 118 determines if the detected person has a corresponding entry (i.e., a matching facial feature vector) in the person-ID dictionary. If so, the detected person is identified, and face-recognition module 118 can output the stored person-ID associated with the matched facial feature vector as person-ID 136 of the detected person. If an embedded vision sensor 202 determines that the detected person is involved in a fall, the embedded vision sensor 202 can generate fall-detection output that includes the identified person-ID 136 of the detected person. However, if the facial feature vector of the detected person doesn't match any stored facial feature vector in the person-ID dictionary, face-recognition module 118 can generate an "unknown person" tag for the detected person.

Note that the above-described distributed fall-detection system design ensures that each embedded fall-detection vision sensor 202 does not transmit any detected face image of any detected person from a captured video image. Instead, all face detection and recognition operations are performed within each embedded fall-detection vision sensor 202, and each embedded fall-detection vision sensor 202 is configured to only transmit an encoded person-ID and sanitized video images to server 204, without including any actual identity of the detected person. This distributed fall-detection system design allows for preserving the privacy of each monitored person by each embedded fall-detection vision sensor to the maximum extent. This distributed fall-detection system design can also minimize the amount of data transmitted over the network and the amount computation performed on the server (e.g., on a cloud server), thereby minimizing the daily operating cost of the disclosed distributed fall-detection system 200.

Figure 7:
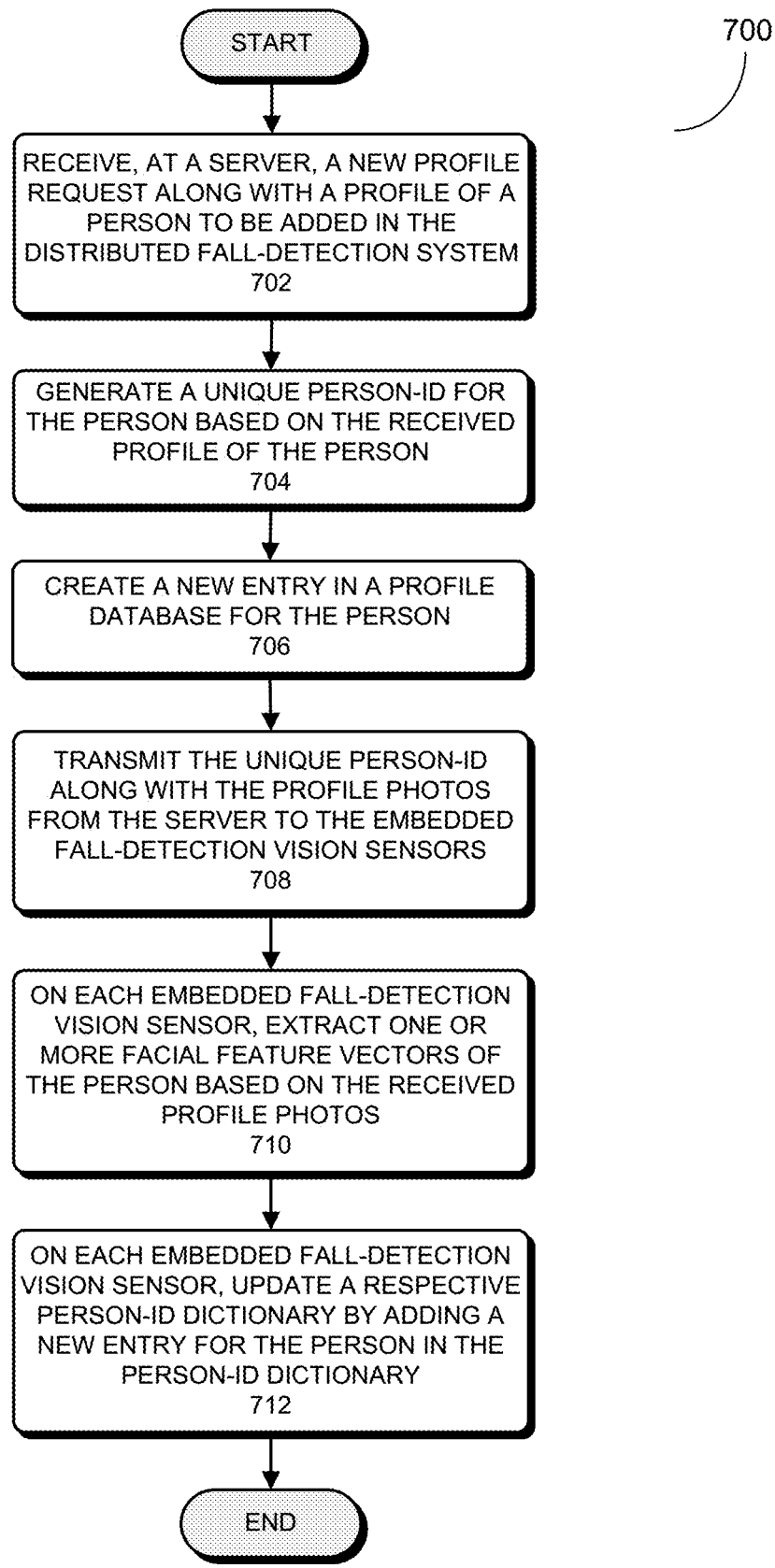
FIG. 7 presents a flowchart illustrating an exemplary process for adding a new profile for a person into the disclosed fall-detection system in accordance with some embodiments described herein.

FIG. 7 presents a flowchart illustrating an exemplary process 700 for adding a new profile for a person into the disclosed distributed fall-detection system 200 in accordance with some embodiments described herein. In one or more embodiments, one or more of the steps in FIG. 7 may be omitted, repeated, and/or performed in a different order. Accordingly, the specific arrangement of steps shown in FIG. 7 should not be construed as limiting the scope of the technique. Note that process 700 can be understood in conjunction with embedded fall-detection system 100 of FIG. 1 and distributed fall-detection system 200 of FIG. 2.

Process 700 may begin when the server (e.g., server 204 in system 200) receives a new profile request along with a profile of a person to be added in the distributed fall-detection system (step 702). As mentioned above, the server can receive the new profile request from the mobile app (e.g., mobile app 212 installed on mobile device 206 in system 200). More specifically, the mobile app can be used to generate the new profile, which includes the identity of the person, and one or more profile photos of the person, and then transmit the new profile request along with the new profile to the server. Next, at the server, process 700 generates a unique person-ID (e.g., a unique integer value) for the person based on the received profile of the person (step 704). For example, the unique person-ID may be created based on the identity of the person (e.g., the name) in the received profile. Process 700 next creates a new entry in a profile database stored on the server for the person, wherein the entry can include the identity, the unique person-ID and the one or multiple profile photos of the person (step 706). Process 700 subsequently transmits the unique person-ID along with the one or more profile photos from the server to the one or multiple embedded fall-detection vision sensors (e.g., embedded vision sensors 202-1 to 202-N) (step 708).

Next, on each embedded vision sensor, process 700 extracts one or more facial feature vectors of the person based on the received one or more profile photos (step 710).

For example, process 700 can use the above-described face-recognition module in conjunction with the face-detection module to generate the facial feature vectors. Process 700 next updates a respective person-ID dictionary stored on each embedded vision sensor by adding a new entry for the person in the person-ID dictionary, wherein the new entry includes both the generated facial feature vectors and the received person-ID of the person (step 712). As mentioned above, after a profile entry is established for the person in the person-ID dictionary, each embedded fall-detection vision sensor can identify and subsequently track the person if that person is detected during a fall-detection process.

Figure 8:
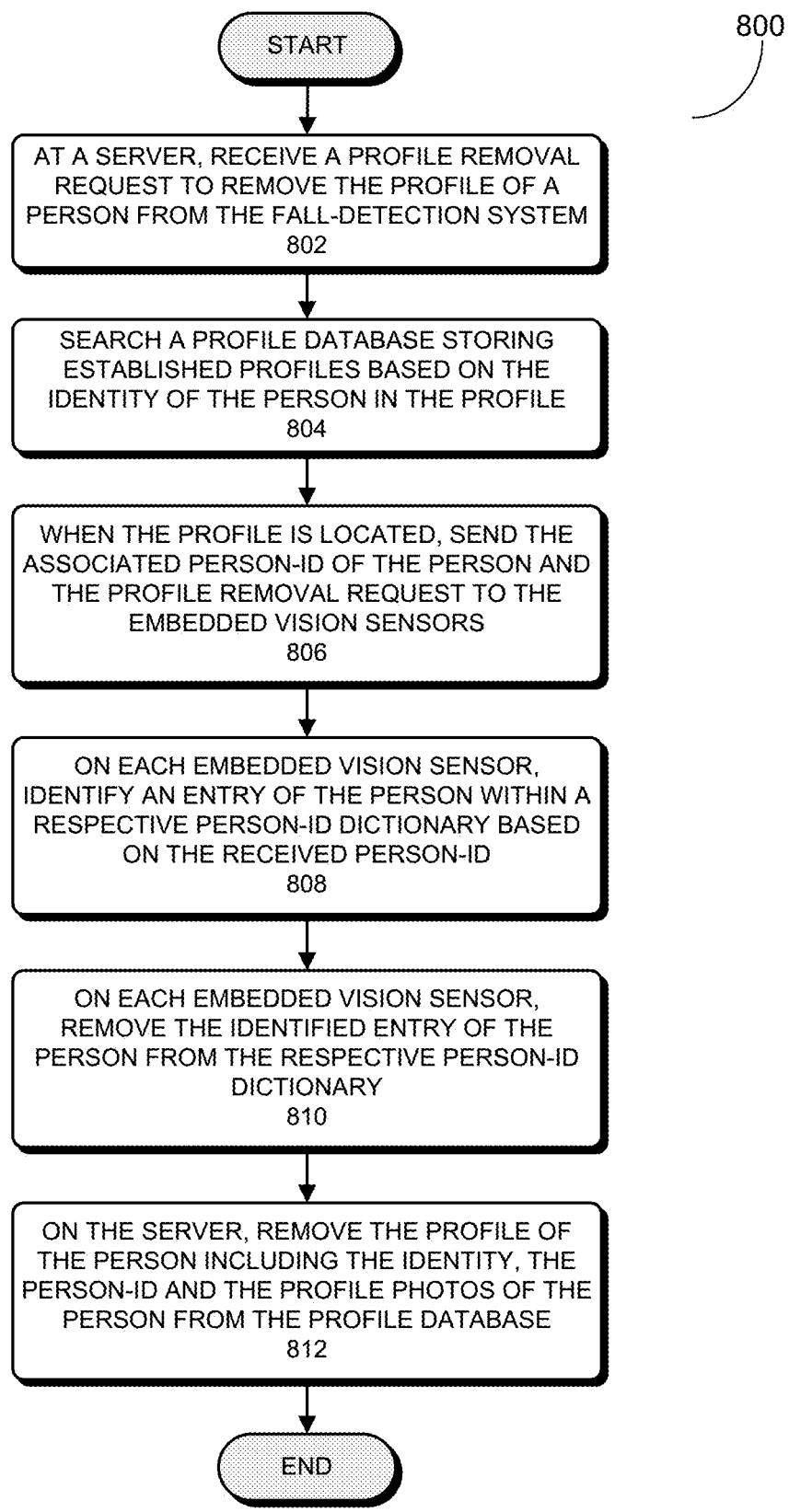
FIG. 8 presents a flowchart illustrating an exemplary process for removing an existing profile of a person from the disclosed fall-detection system in accordance with some embodiments described herein.

Note that in some embodiments, process 700 can be reversed to remove an established entry/profile of a person from the person-ID dictionary. FIG. 8 presents a flowchart illustrating an exemplary process 800 for removing an existing profile of a person from the disclosed distributed fall-detection system 200 in accordance with some embodiments described herein. In one or more embodiments, one or more of the steps in FIG. 8 may be omitted, repeated, and/or performed in a different order. Accordingly, the specific arrangement of steps shown in FIG. 8 should not be construed as limiting the scope of the technique. Note that process 800 can be understood in conjunction with embedded fall-detection system 100 of FIG. 1 and distributed fall-detection system 200 of FIG. 2.

For example, process 800 may begin when the server (e.g., server 204 in system 200) receives a profile removal request to remove the profile of a given person from the distributed fall-detection system (step 802). In some embodiments, the profile removal request can be made using the mobile app, and the server can receive the profile removal request from the mobile app. Note that the profile removal request should include the identity of the person to be removed. When the profile removal request is received at the server, process 800 next searches a profile database storing established profiles of a group of people based on the identity of the person in the profile (step 804). As described above, the stored profiles of the group of people include the established person-IDs of the group of people. Once the profile of the person is located in the profile database, process 800 then sends the associated person-ID of the person along with the profile removal request to the one or multiple embedded fall-detection vision sensors (e.g., embedded vision sensors 202-1 to 202-N) (step 806).

Next, on each embedded vision sensor, process 800 identifies an entry of the person within a respective person-ID dictionary based on the received person-ID of the person (step 808). Process 800 subsequently removes the identified entry of the person from the respective person-ID dictionary (step 810). Next, process 800 may send an acknowledgement to the server indicating that the profile of the person has been successfully removed from the embedded vision sensor. After receiving the acknowledgements from the one or multiple embedded vision sensors at the server, process 800 can remove the profile of the person including the identity, the person-ID and the one or multiple profile photos of the person from the profile database (step 812).

Figure 9:
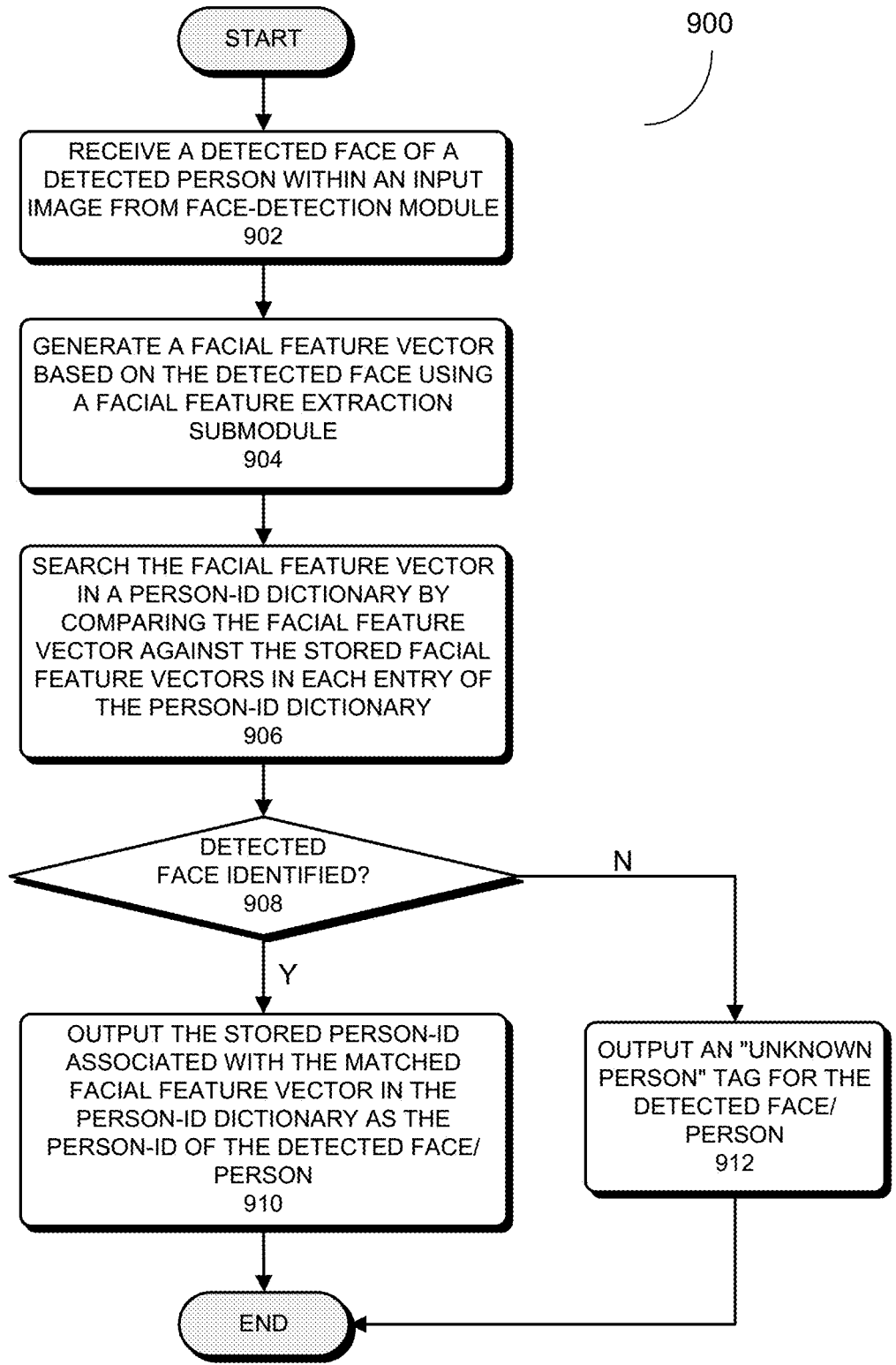
FIG. 9 presents a flowchart illustrating an exemplary process for identifying a detected person by the disclosed embedded fall-detection system in accordance with some embodiments described herein.

FIG. 9 presents a flowchart illustrating an exemplary process 900 for identifying a detected person with the disclosed embedded fall-detection system 100 in accordance with some embodiments described herein. In one or more embodiments, one or more of the steps in FIG. 9 may be omitted, repeated, and/or performed in a different order. Accordingly, the specific arrangement of steps shown in FIG. 9 should not be construed as limiting the scope of the technique. Note that process 900 can be understood in conjunction with embedded fall-detection system 100 of FIG. 1 and in particular face-recognition module 118 within embedded fall-detection system 100. In some embodiments, process 900 can be fully implemented on face-recognition module 118.

Process 900 may begin when face-recognition module 118 receives a detected face of a detected person within an input video image 104 from face-detection module 116 (step 902). Process 900 next generates a facial feature vector based on the detected face using a facial feature extraction submodule within face-recognition module 118 (step 904). In various embodiments, this facial feature vector can be a 1-D facial feature vector, a 2-D facial feature vector, or a 3-D facial feature vector. Next, process 900 searches the generated facial feature vector in a person-ID dictionary, such as person-ID dictionary 150 by comparing the facial feature vector against the stored facial feature vectors in each entry of the person-ID dictionary (step 906). In some embodiments, the person-ID dictionary is stored in a memory within embedded fall-detection system 100. Next, process 900 determines if the detected face has a corresponding entry in the person-ID dictionary based on whether a matched facial feature vector can be found (step 908). If so, the detected face/person is identified, and process 900 can output the stored person-ID associated with the matched facial feature vector in the person-ID dictionary as the person-ID of the detected face/person (step 910). Subsequently, if the embedded fall-detection system determines that the detected person is involved in a fall, the embedded fall-detection system can output the fall alarm along with the identified person-ID of the detected person. However, if the facial feature vector of the detected face/person doesn't match any stored facial feature vector in the person-ID dictionary, process 900 can output an "unknown person" tag for the detected face/person (step 912).

Privacy-Preserving Design

The disclosed embedded fall-detection system 100 and distributed fall-detection system 200 are designed to preserve the privacies of each person/user captured by each embedded fall-detection vision sensor 202 in the disclosed distributed fall-detection system 200. In some embodiments, the privacy-preserving nature of the disclosed embedded fall-detection system 100 and distributed fall-detection system 200 is achieved by performing some or all of the above-described fall-detection-related operations on input video images 104 in-situ inside each standalone embedded vision sensor 202. Moreover, after processing the captured video images in-situ, each embedded vision sensor 202 can only transmit sanitized video images along with fall alarms to server 204 (e.g., by transmitting only the keypoints/skeleton/stick figure representations of each detected person instead of the actual cropped images of the detected person).

In some embodiments, various features extracted from a sequence of most recent video frames can be stored in a memory buffer of each embedded vision sensor 202. These stored features can include human keypoints, skeleton diagrams/stick figures, and face recognition results including person-IDs 136 from each processed video frame. In some embodiments, these stored features can be used to reconstruct a sanitized video clip of the most recent N seconds (e.g., N=5~15) of the captured video frames. Hence, once a fall is detected by the associated embedded fall-detection system 100, the given embedded vision sensor 202 can send a fall alarm/notification 140-1 along with the reconstructed sanitized video clip 140-2 of the most recent N seconds (e.g., 10 seconds) of the captured video frames to server 204.

In some embodiments, reconstructing a sanitized video clip can include first identifying a common background image for the sequence of original video frames, wherein the common background image is a static image that does not include the detected person. For example, the common background image can be extracted from a static video image before the detected person enters the camera view. Next, the sequence of sanitized video frames can be generated by directly superimposing the sequence of skeleton diagrams of the detected person corresponding to the sequence of original video frames onto the common background image. For example, to generate a sanitized video frame i in the sanitized video clip, we can superimpose the skeleton diagram i generated from frame i in the sequence of original video frames directly onto the common background image. Note that this sanitized video reconstruction technique can have lower computational and storage costs than directly processing/modifying the original video frames.

Similarly, to preserve the privacy of a person when a live streaming is requested for the person, the disclosed embedded vision sensors 202 do not transmit the original live video images to server 204 or to mobile devices 212. Instead, each embedded fall-detection vision sensor 202 is configured to send sanitized live video images (e.g., the keypoints or the skeleton representations of the person). In some embodiments, the amount of information that can be included in the sanitized video images can be tailored based on the specific privacy needs of a given user.

For example, in a highly-restrictive privacy-preserving mode, embedded fall-detection system 100 can be configured to only include the skeleton representations/stick figures of the people detected in each video frame, which is sufficient to show how a person takes a fall, but will not include any human identity information and background information in the transmitted video frame. Alternatively, in a less restrictive privacy-preserving mode, in addition to transmitting skeleton representations/stick figures of the detected people to the server, embedded fall-detection system 100 can be configured to also transmit some segmented background masks (e.g., generated by scene-segmentation module 112) of the captured scene/video frames. For example, the segmented background masks can include labeled regions corresponding to non-human objects detected in the scene to help understand the scene or the detected fall, such as beds and sofas in the scene relative to the person. However, these segmented background masks do not show the original images of these identified objects.

In another exemplary privacy-preserving mode, a transmitted video can include the original background images in the video. However, by sending the human keypoints or the associated skeleton representations instead of the original video images of the detected persons, the disclosed fall-detection systems 100 and 200 can effectively preserve each detected person's privacy, making it suitable for people monitoring in bedrooms and bathrooms. In some embodiments however, when proof of human identity is required, e.g., for legal purposes, embedded fall-detection system 100 can also be configured to transmit a region in the video images corresponding to the head and the face of a given person, but the body portion of the person can still be represented by the associated skeleton representation in the transmitted video images.

Embedded Vision System—Hardware Environment

Figure 10:
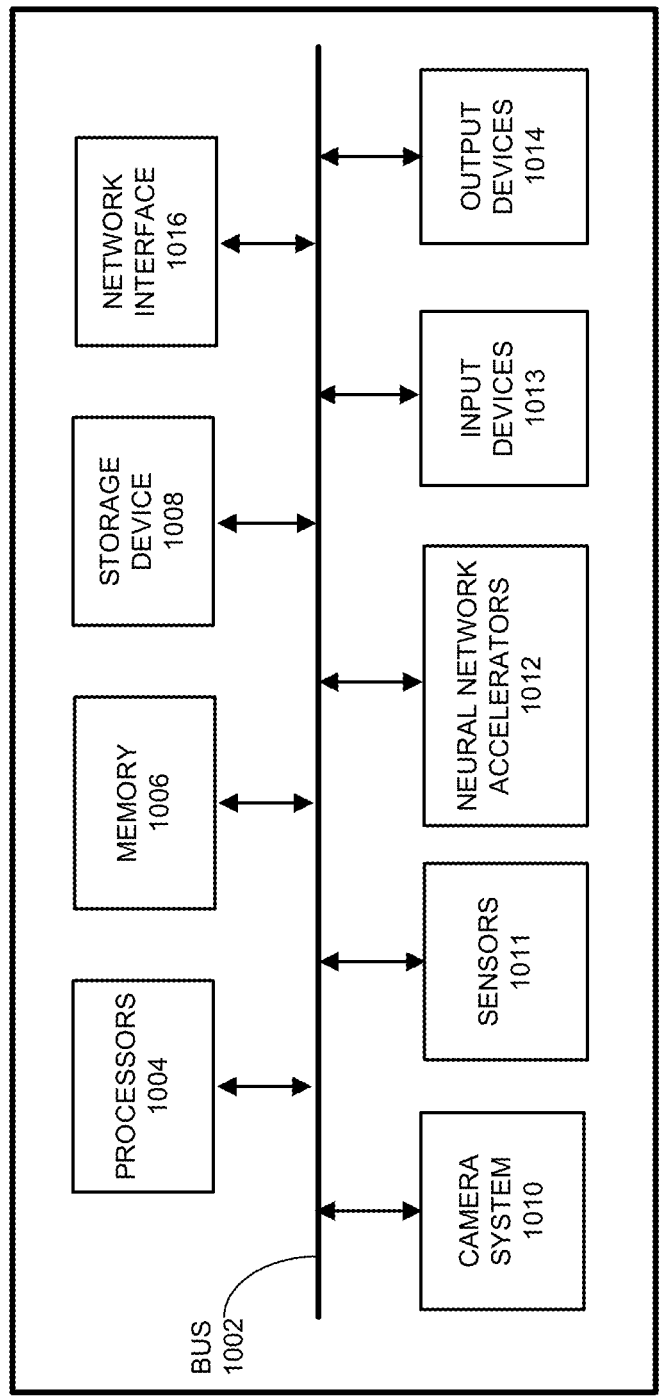
FIG. 10 illustrates an exemplary hardware environment for the disclosed embedded fall-detection system in accordance with some embodiments described herein.

FIG. 10 illustrates an exemplary hardware environment 1000 for the disclosed embedded fall-detection system 100 of FIG. 1 in accordance with some embodiments described herein. Note that hardware environment 1000 can be used to implement each of the one or multiple embedded fall-detection vision sensors 202-1, 202-2, . . . , and 202-N within distributed fall-detection system 200. As can be seen in FIG. 10, hardware environment 1000 can include a bus 1002, one or more processors 1004, a memory 1006, a storage device 1008, a camera system 1010, sensors 1011, one or more neural network accelerators 1012, one or more input devices 1013, one or more output devices 1014, and a network interface 1016.

Bus 1002 collectively represents all system, peripheral, and chipset buses that communicatively couple the various components of hardware environment 1000. For instance, bus 1002 communicatively couples processors 1004 with memory 1006, storage device 1008, camera system 1010, sensors 1011, neural network accelerators 1012, input devices 1013, output devices 1014, and network interface 1016.

From memory 1006, processors 1004 retrieves instructions to execute and data to process in order to control various components of hardware environment 1000, and to execute various functionalities described in this patent disclosure including the various disclosed functions of the various functional modules in the disclosed embedded fall-detection system 100, including but not limited to: pose-estimation module 106, action-recognition module 108, fall-detection module 110 including state machine 120 and invalid pose filter 138, scene-segmentation module 112, face-detection module 116, face-recognition module 118, and the ADL statistics module (not shown). Processors 1004 can include any type of processor, including, but not limited to, one or more central processing units (CPUs), one or more microprocessors, one or more graphic processing units (GPUs), one or more tensor processing units (TPUs), one or more digital signal processors (DSPs), one or more field-programmable gate arrays (FPGAs), one or more application-specific integrated circuit (ASICs), a personal organizer, a device controller and a computational engine within an appliance, and any other processor now known or later developed. Furthermore, a given processor 1004 can include one or more cores. Moreover, a given processor 1004 itself can include a cache that stores code and data for execution by the given processor 1004.

Memory 1006 can include any type of memory that can store code and data for execution by processors 1004, neural network accelerators 1012, and some other processing modules of hardware environment 1000. This includes but not limited to, dynamic random access memory (DRAM), static random access memory (SRAM), flash memory, read only memory (ROM), and any other type of memory now known or later developed.

Storage device 1008 can include any type of non-volatile storage device that can be integrated with hardware environment 1000. This includes, but is not limited to, magnetic, optical, and magneto-optical storage devices, as well as storage devices based on flash memory and/or battery-backed up memory. In some implementations, various programs for implementing the various disclosed functions of the various disclosed modules in the disclosed embedded fall-detection system 100, including pose-estimation module 106, action-recognition module 108, fall-detection module 110 including state machine 120 and invalid pose filter 138, scene-segmentation module 112, face-detection module 116, face-recognition module 118, and the ADL statistics module (not shown), are stored in memory 1006 and storage device 1008.

Bus 1002 is also coupled to camera system 1010. Camera system 1010 is configured to capture a sequence of video images at predetermined resolutions and couple the captured video images to various components within hardware environment 1000 via bus 1002, such as to memory 1006 for buffering and to processors 1004 and neural network accelerators 1012 for various deep-learning and neural network-based operations. Camera system 1010 can include one or more digital cameras. In some embodiments, camera system 1010 includes one or more digital cameras equipped with wide-angle lenses. The captured images by camera system 1010 can have different resolutions including high-resolutions such as at 1280×720p, 1920×1080p or other high resolutions.

In some embodiments, neural network accelerators 1012 can include any type of microprocessor designed as hardware acceleration for executing AI-based and deep-learning-based programs and models, and in particular various deep learning neural networks such as various CNN and RNN frameworks mentioned in this disclosure. Neural network accelerators 1012 can perform the intended functions of each of the described deep-learning-based modules within the disclosed embedded fall-detection system 100, i.e., pose-estimation module 106, action-recognition module 108, fall-detection module 110, scene-segmentation module 112, face-detection module 116, face-recognition module 118, and the ADL statistics module. Examples of neural network accelerators 1012 can include but are not limited to: the dual-core ARM Mali-G71 GPU, dual-core Neural Network Inference Acceleration Engine (NNIE), and the quad-core DSP module in the HiSilicon Hi3559A SoC.

Bus 1002 also connects to input devices 1013 and output devices 1014. Input devices 1013 enable the user to communicate information and select commands to hardware environment 1000. Input devices 1013 can include, for example, a microphone, alphanumeric keyboards and pointing devices (also called "cursor control devices").

Hardware environment 1000 also includes a set of sensors 1011 coupled to bus 1002 for collection environment data in assisting various fall-detection functionalities of the disclosed embedded fall-detection system 100. Sensors 1011 can include a motion sensor, an ambient light sensor, and an infrared sensor such as a passive infrared sensor (PIR) sensor. To enable the functionality of a PIR sensor, hardware environment 1000 can also include an array of IR emitters.

Output devices 1014 which are also coupled to bus 1002, enable for example, the display of the results generated by processors 1004 and neural network accelerators 1012. Output devices 1014 include, for example, display devices, such as cathode ray tube displays (CRT), light-emitting diode displays (LED), liquid crystal displays (LCD), organic light-emitting diode displays (OLED), plasma displays, or electronic paper. Output devices 1014 can also include audio output devices such as a speaker. Output devices 1014 can additionally include one or more LED indicators.

Finally, as shown in FIG. 10, bus 1002 also couples hardware environment 1000 to a network (not shown) through a network interface 1016. In this manner, hardware environment 1000 can be a part of a network, such as a local area network ("LAN"), a Wi-Fi network, a wide area network ("WAN"), or an Intranet, or a network of networks, such as the Internet. Hence, network interface 1016 can include a Wi-Fi network interface. Network interface 1016 can also include a Bluetooth interface. Any or all components of hardware environment 1000 can be used in conjunction with the subject disclosure.

In a particular embodiment of hardware environment 1000, hardware environment 1000 is implemented as an embedded fall-detection vision sensor which includes at least the following components: one or more cameras; multiple CPUs; multiple GPUs; multiple neural network accelerators (e.g., NNIE accelerators); multiple DSPs; multiples memory modules; a storage device; a WiFi module; a Bluetooth module; a microphone; a speaker; a display interface; multiple sensors including a motion sensor, an ambient light sensor, and an IR sensor; and finally multiple LED indicators.

Task Scheduling and Low-Level Optimizations

Figure 11:
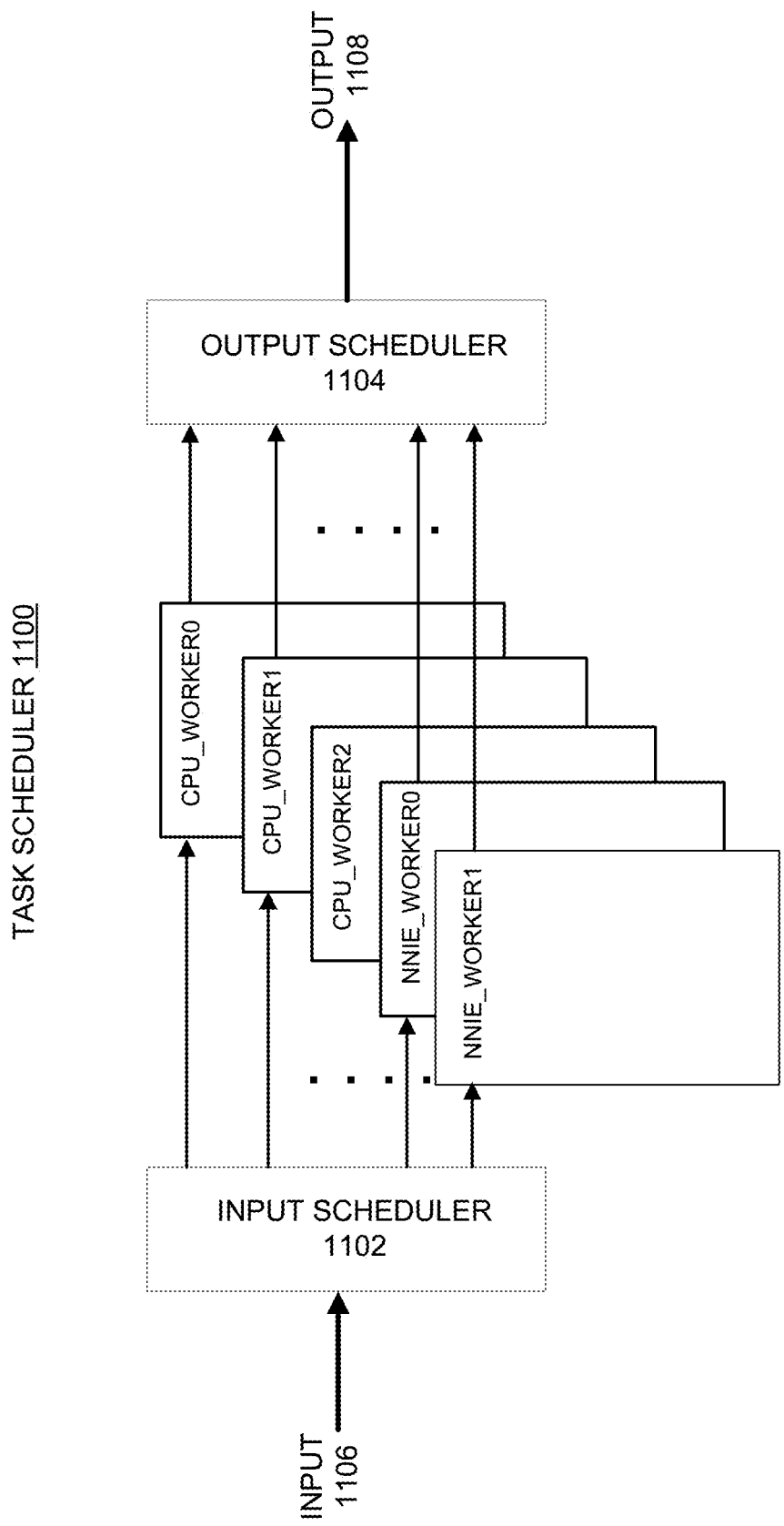
FIG. 11 shows an exemplary task scheduler for executing the various fall-detection functionalities of the disclosed embedded fall-detection system in accordance with some embodiments described herein.

In some embodiments, to take full advantage of the available processing power of hardware environment 1000, a customized task scheduler can be designed to utilize multiple hardware resources such as ARM CPU and NNIE accelerator in parallel to achieve a maximum processing throughput. FIG. 11 shows an exemplary task scheduler 1100 for executing the various disclosed fall-detection functionalities of embedded fall-detection system 100 in accordance with some embodiments described herein.

As can be seen in FIG. 11, task scheduler 1100 can include an input scheduler 1102 and an output scheduler 1104. Each task scheduler 1100 can instantiate an arbitrary number of workers to complete the same task in parallel, e.g., three CPU workers: CPU_Worker0, CPU_Worker1, and CPU_Worker2, and two NNIE workers: NNIE_Worker0 and NNIE_Worker0. Furthermore, each worker in task scheduler 1100 can use a different hardware resource (i.e., either the CPU or the NNIE accelerator) offered by hardware environment 1000. In some embodiments, input scheduler 1102 can be configured to receive raw video images as input 1106, and schedule the set of workers to perform the following two streams of tasks on the input video images: (1) the pose-estimation tasks followed by the action-recognition tasks and the fall-detection tasks, and subsequently generating fall detection output including fall alarms, sanitized video clips and/or ADLs as output 1108; and (2) face-detection tasks followed by face-recognition tasks, and subsequently generating person-IDs as output 1108. Moreover, input scheduler 1102 and the output scheduler 1104 of task scheduler 1100 can be configured to ensure that the order in output 1108 (e.g., the fall-detection alarms, sanitized video clips, and ADLs) matches the order of the raw video images in input 1106.

Figure 12:
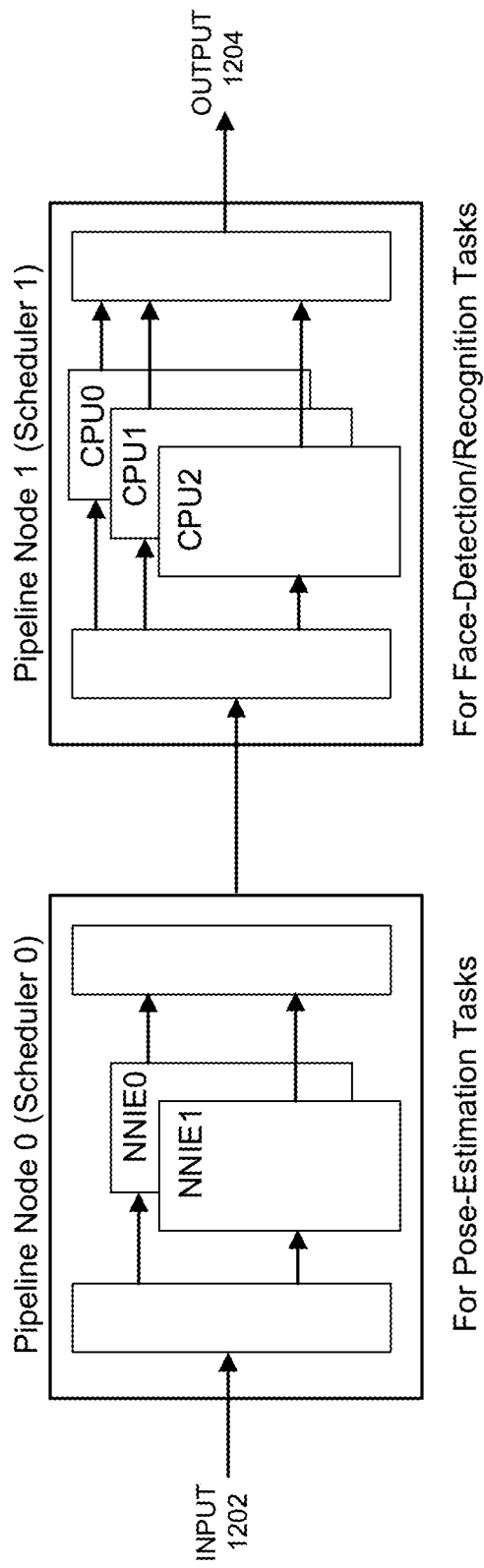
FIG. 12 illustrates an exemplary processing pipeline comprising two task scheduler nodes based on the disclosed task scheduler coupled in series in accordance with some embodiments described herein.

Note that multiple instances of task scheduler 1100 can be chained/coupled in series to form a processing pipeline, with each node (i.e., each instance of task scheduler 1100) of the processing pipeline performing a specific task. For example, FIG. 12 illustrates an exemplary processing pipeline 1200 comprising two task scheduler nodes based on the above-described task scheduler coupled in series in accordance with some embodiments described herein. As shown in FIG. 12, the first scheduler node (i.e., Node 0) includes two NNIE workers (NNIE0 and NNIE1) configured to perform the above-described pose estimation tasks, whereas the second scheduler node (i.e., Node 1) employs three CPU cores (CPU0, CPU1, and CPU2) in parallel to perform the above-described face detection and recognition tasks. Node 0/Scheduler 0 can receive raw video images as input 1202, whereas Node 1/Scheduler 1 can generate certain fall detection output such as person-IDs as output 1204.

In some embodiments, to speed up the various neural network modules used by the disclosed embedded fall-detection system, certain computationally-intensive layers within a given neural network module can be redesigned using ARM NEON instructions.

Note that while the various techniques for modifying and optimizing existing models and frameworks to implement the disclosed embedded fall-detection system 100 and the various task scheduling techniques are described in the scope fall-detection systems, the concepts of the disclosed modifications and optimization and task scheduling techniques can be applied to other similar embedded systems, not just fall-detection systems.

Figure 13:
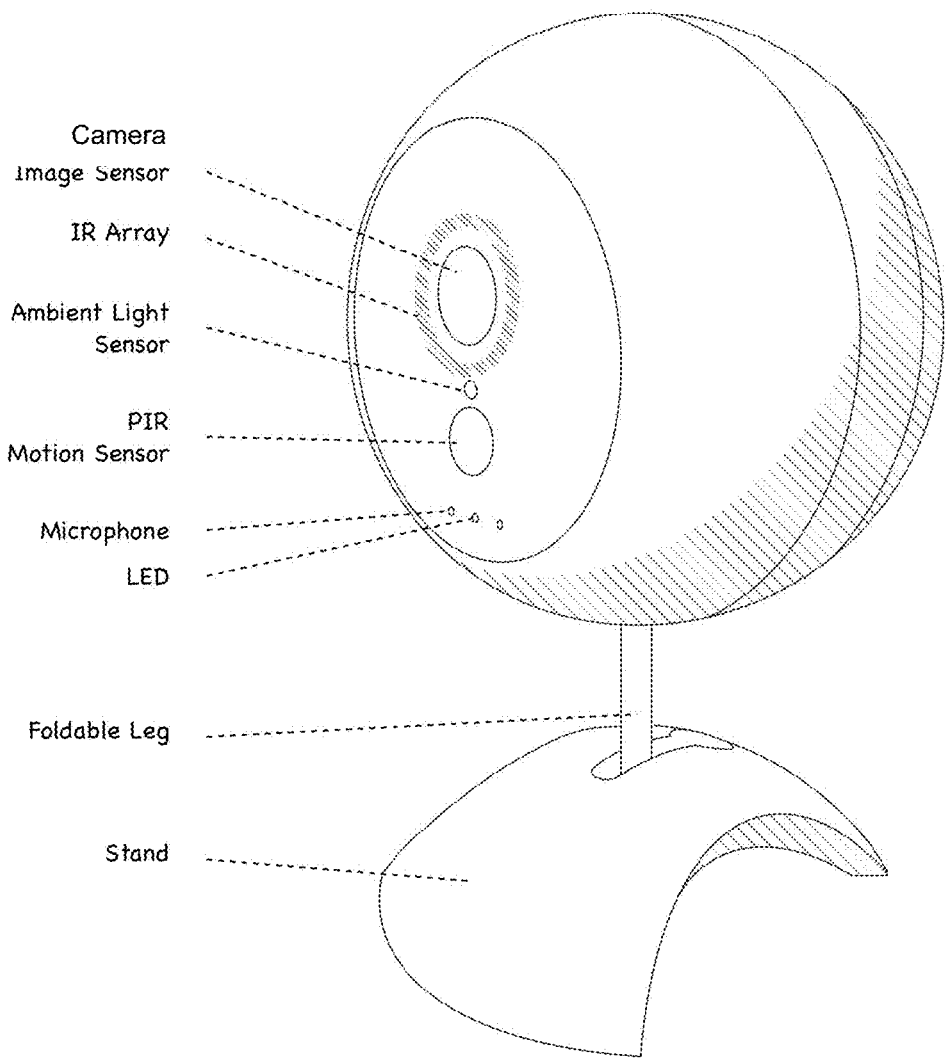
FIG. 13 illustrates an exemplary exterior design of the disclosed embedded fall-detection vision sensor which implements the disclosed embedded fall-detection system of FIG. 1 in accordance with some embodiments described herein.

FIG. 13 illustrates an exemplary exterior design of the disclosed embedded fall-detection vision sensor 1300 which implements the disclosed embedded fall-detection system 100 in accordance with some embodiments described herein. More specifically, FIG. 13 shows a perspective view of the embedded fall-detection vision sensor 1300. Note that the front surface of the embedded fall-detection vision sensor 1300 includes various sensors and lights. The large circle above the ambient light sensor is the location of the camera that captures the actual images. In some embodiments, inside the body of the embedded fall-detection vision sensor 1300 includes at least the following components: one or more cameras, multiple CPUs; multiple GPUs; multiple neural network accelerators; multiple DSPs; multiples memory modules; a storage device; a WiFi module; a Bluetooth module; a microphone; a speaker; a display interface; multiple sensors including a motion sensor, an ambient light sensor, and an IR sensor; and finally multiple LED indicators.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

While this patent document contains many specifics, these should not be construed as limitations on the scope of any invention or of what may be claimed, but rather as descriptions of features that may be specific to particular embodiments of particular inventions. Certain features that are described in this patent document and attached appendix in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendix should not be understood as requiring such separation in all embodiments.

Only a few implementations and examples are described and other implementations, enhancements and variations can be made based on what is described and illustrated in this patent document and attached appendix.

What is claimed is:

1. A method of detecting personal fall while preserving the privacy of a detected person, comprising:
  receiving a sequence of video images comprising a person being monitored;
  processing the sequence of video images by, for each video image in the sequence of video images:
    detecting the person in the video image; and
    extracting a skeletal figure of the detected person by identifying a set of human keypoints from the detected person;
  processing the sequence of skeletal figures corresponding to the sequence of video images by labeling each skeletal figure in the sequence of skeletal figures with an action among a set of predetermined actions; and generating a fall/non-fall decision for the detected person based on the set of action labels corresponding to the sequence of video images.

2. The method of claim 1, wherein the method further comprises generating a privacy-preserving video clip of the detected person by replacing the detected person within each video image with the corresponding extracted skeletal figure.

3. The method of claim 1, wherein prior to labeling each skeletal figure with an action label, the method further comprises estimating a pose of the detected person within each video image based on the set of locations of the set of human keypoints of the detected person in the video image.

4. The method of claim 3, wherein labeling each skeletal figure in the sequence of skeletal figures with an action label comprises:
   feeding the set of human keypoints of the detected person in the video image into a machine-learning-based action classifier pre-trained to classify a pose of the detected person into one of the set of predetermined actions; and
   classifying the estimated pose of the detected person in the video image into an action among the set of predetermined actions based on a set of computed probabilities corresponding to the set of predetermined actions.

5. The method of claim 4, wherein the set of predetermined actions includes a first category of actions and a second category of actions, and wherein classifying the estimated pose of the detected person into an action among the set of predetermined actions includes:
   classifying the estimated pose of the detected person into either the first category of actions or the second category of actions; and
   for the classified first or second category of actions, further classifying the estimated pose of the detected person into a predetermined action among the classified category of actions.

6. The method of claim 5,
   wherein the first category of actions includes a predetermined set of dangerous actions; and
   wherein the second category of actions includes a predetermined set of normal actions.

7. The method of claim 5,
   wherein the predetermined set dangerous actions includes one or more of: a lying action and a struggling action; and
   wherein the predetermined set of normal actions includes one or more of: a standing action, one or more types of sitting actions, a bending action, and a squatting action.

8. The method of claim 1, wherein generating a fall/non-fall decision for the detected person based on the set of action labels includes:
   aggregating the sequence of labeled actions for the detected person corresponding to the sequence of video images; and
   processing the sequence of labeled actions to determine if a fall has occurred.

9. An apparatus for detecting personal fall while preserving the privacy of a detected person, comprising:
   one or more processors; and
   a memory coupled to the one or more processors, wherein the memory stores a set of instructions that, when executed by the one or more processors, cause the apparatus to:
      receive a sequence of video images comprising a person being monitored;
      process the sequence of video images by, for each video image in the sequence of video images:
         detecting the person in the video image; and
         extracting a skeletal figure of the detected person by identifying a set of human keypoints from the detected person;
      process the sequence of skeletal figures corresponding to the sequence of video images by labeling each skeletal figure in the sequence of skeletal figures with an action among a set of predetermined actions; and
      generate a fall/non-fall decision for the detected person based on the set of action labels corresponding to the sequence of video images.

10. The apparatus of claim 9, wherein the memory further stores instructions that, when executed by the one or more processors, cause the apparatus to generate a privacy-preserving video clip of the detected person by replacing the detected person within each video image with the corresponding extracted skeletal figure.

11. The apparatus of claim 9, wherein prior to labeling each skeletal figure with an action label, the memory further stores instructions that, when executed by the one or more processors, cause the apparatus to estimate a pose of the detected person within each video image based on the set of locations of the set of human keypoints of the detected person in the video image.

12. The apparatus of claim 11, wherein the memory further stores instructions that, when executed by the one or more processors, cause the apparatus to label each skeletal figure in the sequence of skeletal figures with an action label by:
   feeding the set of human keypoints of the detected person in the video image into a machine-learning-based action classifier pre-trained to classify a pose of the detected person into one of the set of predetermined actions; and
   classifying the estimated pose of the detected person in the video image into an action among the set of predetermined actions based on a set of computed probabilities corresponding to the set of predetermined actions.

13. The apparatus of claim 12, wherein the set of predetermined actions includes a first category of actions and a second category of actions, and wherein the memory further stores instructions that, when executed by the one or more processors, cause the apparatus to classify the estimated pose of the detected person into an action among the set of predetermined actions by:
   classifying the estimated pose of the detected person into either the first category of actions or the second category of actions; and
   for the classified first or second category of actions, further classifying the estimated pose of the detected person into a predetermined action among the classified category of actions.

14. The apparatus of claim 13,
   wherein the first category of actions includes a predetermined set of dangerous actions; and
   wherein the second category of actions includes a predetermined set of normal actions.

15. The apparatus of claim 13,
   wherein the predetermined set dangerous actions includes one or more of: a lying action and a struggling action; and wherein the predetermined set of normal actions includes one or more of: a standing action, one or more types of sitting actions, a bending action, and a squatting action.

16. The apparatus of claim 9, wherein the memory further stores instructions that, when executed by the one or more processors, cause the apparatus to generate a fall/non-fall decision for the detected person based on the set of action labels by:
   aggregating the sequence of labeled actions for the detected person corresponding to the sequence of video images; and
   processing the sequence of labeled actions to determine if a fall has occurred.

17. A fall-detection system, comprising:
   one or more cameras configured to capture a sequence of video images including a person;
   one or more processors;
   a memory coupled to the one or more processors and storing instructions that, when executed by the one or more processors, cause the system to:
      receive a sequence of video images comprising a person being monitored;
      process the sequence of video images by, for each video image in the sequence of video images:
         detecting the person in the video image; and
         extracting a skeletal figure of the detected person by identifying a set of human keypoints from the detected person;
      process the sequence of skeletal figures corresponding to the sequence of video images by labeling each skeletal figure in the sequence of skeletal figures with an action among a set of predetermined actions; and
      generate a fall/non-fall decision for the detected person based on the set of action labels corresponding to the sequence of video images.

18. The fall-detection system of claim 17, wherein the memory further stores instructions that, when executed by the one or more processors, cause the system to generate a privacy-preserving video clip of the detected person by replacing the detected person within each video image with the corresponding extracted skeletal figure.

19. The fall-detection system of claim 17, wherein prior to labeling each skeletal figure with an action label, the memory further stores instructions that, when executed by the one or more processors, cause the system to estimate a pose of the detected person within each video image based on the set of locations of the set of human keypoints of the detected person in the video image.

20. The fall-detection system of claim 19, wherein the set of predetermined actions includes a first category of actions and a second category of actions, and wherein the memory further stores instructions that, when executed by the one or more processors, cause the system to classify the estimated pose of the detected person into an action among the set of predetermined actions by:
   classifying the estimated pose of the detected person into either the first category of actions or the second category of actions; and
   for the classified first or second category of actions, further classifying the estimated pose of the detected person into a predetermined action among the classified category of actions.

* * * * *